United States Patent
Ferren et al.

(10) Patent No.: US 8,679,101 B2
(45) Date of Patent: Mar. 25, 2014

(54) METHOD AND SYSTEM FOR TEMPORARY HAIR REMOVAL

(75) Inventors: Bran Ferren, Beverly Hills, CA (US); Muriel Y. Ishikawa, Livermore, CA (US); Edward K. Y. Jung, Bellevue, WA (US); Nathan P. Myhrvold, Medina, WA (US); Clarence T. Tegreene, Bellevue, WA (US); Lowell L. Wood, Jr., Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 2872 days.

(21) Appl. No.: 11/073,361

(22) Filed: Mar. 4, 2005

(65) Prior Publication Data

US 2006/0200116 A1    Sep. 7, 2006

(51) Int. Cl.
*A61B 18/18* (2006.01)

(52) U.S. Cl.
USPC .......... 606/9; 606/2; 606/10; 606/13; 607/88; 128/898

(58) Field of Classification Search
USPC ............................................................ 606/9
See application file for complete search history.

(56) References Cited

U.S. PATENT DOCUMENTS

| | | | |
|---|---|---|---|
| 3,685,051 A | 8/1972 | Wells | |
| 4,214,490 A | 7/1980 | Chizek | |
| 4,880,001 A | 11/1989 | Weinberg | |
| 4,898,192 A | 2/1990 | Cohen | |
| 4,979,935 A | 12/1990 | Lindmayer | |
| 5,071,417 A | 12/1991 | Sinofsky | |
| 5,226,907 A | 7/1993 | Tankovich | |
| 5,279,284 A | 1/1994 | Fenn | |
| 5,425,728 A | 6/1995 | Tankovich | |
| 5,470,351 A | 11/1995 | Ross et al. | |
| 5,497,227 A | 3/1996 | Takeuchi et al. | |
| 5,501,680 A * | 3/1996 | Kurtz et al. | 606/9 |
| 5,586,981 A | 12/1996 | Hu | |
| 5,606,798 A | 3/1997 | Kelman | |
| 5,630,811 A | 5/1997 | Miller | |
| 5,743,899 A | 4/1998 | Zinreich | |
| 5,757,523 A | 5/1998 | Wood et al. | |
| 5,820,625 A * | 10/1998 | Izawa et al. | 606/9 |
| 5,833,649 A | 11/1998 | Atef | |
| 5,846,080 A * | 12/1998 | Schneider | 433/215 |
| 5,849,029 A | 12/1998 | Eckhouse et al. | |
| 5,853,407 A | 12/1998 | Miller | |

(Continued)

FOREIGN PATENT DOCUMENTS

WO    WO 00/62700    10/2000

OTHER PUBLICATIONS

"Hair density"; keratin.com; pp. 1-4; located at: http://www.keratin.com/aa/aa014.shtml; printed on Jan. 18, 2005.

(Continued)

*Primary Examiner* — Lynsey Crandall
(74) *Attorney, Agent, or Firm* — Suiter Swantz pc llo

(57) ABSTRACT

Embodiments of methods and systems for hair treatment are disclosed. According to various embodiments, light is used to shave, trim, or otherwise modify hair shafts.

15 Claims, 20 Drawing Sheets

(56) References Cited

U.S. PATENT DOCUMENTS

| | | | |
|---|---|---|---|
| 5,860,967 A | 1/1999 | Zavislan et al. | |
| 5,865,832 A | 2/1999 | Knopp et al. | |
| 5,871,480 A | 2/1999 | Tankovich | |
| 5,879,376 A | 3/1999 | Miller | |
| 5,914,255 A | 6/1999 | Grae | |
| 5,968,097 A | 10/1999 | Frechet et al. | |
| 5,990,193 A | 11/1999 | Russell et al. | |
| 6,013,122 A | 1/2000 | Klitzman et al. | |
| 6,050,990 A | 4/2000 | Tankovich et al. | |
| 6,063,074 A | 5/2000 | Tankovich | |
| 6,074,382 A * | 6/2000 | Asah et al. | 606/9 |
| 6,090,790 A | 7/2000 | Eriksson | |
| 6,119,038 A | 9/2000 | Cook | |
| 6,152,917 A | 11/2000 | Tankovich | |
| 6,162,211 A | 12/2000 | Tankovich et al. | |
| 6,168,590 B1 * | 1/2001 | Neev | 606/9 |
| 6,171,302 B1 | 1/2001 | Talpalriu et al. | |
| 6,192,890 B1 | 2/2001 | Levy et al. | |
| 6,215,893 B1 | 4/2001 | Leshem et al. | |
| 6,221,095 B1 | 4/2001 | Van Zuylen et al. | |
| 6,235,015 B1 * | 5/2001 | Mead et al. | 606/9 |
| 6,263,762 B1 | 7/2001 | Zeitler | |
| 6,267,724 B1 | 7/2001 | Taylor | |
| 6,267,771 B1 | 7/2001 | Tankovich et al. | |
| 6,273,884 B1 | 8/2001 | Altshuler et al. | |
| 6,306,128 B1 | 10/2001 | Waldman et al. | |
| 6,315,480 B1 | 11/2001 | Martel et al. | |
| 6,341,831 B1 | 1/2002 | Weber et al. | |
| 6,355,054 B1 | 3/2002 | Neuberger | |
| 6,358,242 B1 | 3/2002 | Cecchetti | |
| 6,406,474 B1 * | 6/2002 | Neuberger et al. | 606/9 |
| 6,413,255 B1 | 7/2002 | Stern | |
| 6,420,431 B1 | 7/2002 | Johnson | |
| 6,428,532 B1 * | 8/2002 | Doukas et al. | 606/9 |
| 6,457,585 B1 | 10/2002 | Huffer et al. | |
| 6,461,594 B1 | 10/2002 | Chaiken et al. | |
| 6,508,813 B1 | 1/2003 | Altshuler | |
| 6,511,475 B1 | 1/2003 | Altshuler et al. | |
| 6,514,243 B1 | 2/2003 | Eckhouse et al. | |
| 6,533,744 B1 | 3/2003 | Stanish et al. | |
| 6,569,157 B1 | 5/2003 | Shain et al. | |
| 6,584,359 B1 | 6/2003 | Motoi | |
| 6,611,706 B2 | 8/2003 | Avrahami et al. | |
| 6,629,974 B2 | 10/2003 | Penny et al. | |
| 6,660,000 B2 | 12/2003 | Neuberger et al. | |
| 6,662,036 B2 | 12/2003 | Cosman | |
| 6,685,719 B2 | 2/2004 | Matera, Jr. | |
| 6,699,509 B1 | 3/2004 | Melinte et al. | |
| 6,717,102 B2 | 4/2004 | Neev et al. | |
| 6,743,222 B2 | 6/2004 | Durkin et al. | |
| 6,749,602 B2 | 6/2004 | Sierra et al. | |
| 6,757,106 B2 | 6/2004 | Kusuyama | |
| 6,757,309 B1 | 6/2004 | Karpinski | |
| 6,758,845 B1 | 7/2004 | Weckwerth et al. | |
| 6,764,493 B1 | 7/2004 | Weber et al. | |
| 6,766,199 B2 | 7/2004 | Cook et al. | |
| 6,773,698 B1 | 8/2004 | Melinte et al. | |
| 6,790,205 B1 * | 9/2004 | Yamazaki et al. | 606/9 |
| 6,791,531 B1 | 9/2004 | Johnston et al. | |
| 6,800,122 B2 | 10/2004 | Anderson et al. | |
| 6,814,760 B2 | 11/2004 | Anderson et al. | |
| 6,816,528 B1 | 11/2004 | Kneissl et al. | |
| 6,829,265 B2 | 12/2004 | Nakatsuka et al. | |
| 6,834,070 B2 | 12/2004 | Zapata | |
| 6,881,249 B2 | 4/2005 | Anderson et al. | |
| 6,997,923 B2 | 2/2006 | Anderson et al. | |
| 7,066,929 B1 | 6/2006 | Azar et al. | |
| 7,108,690 B1 * | 9/2006 | Lefki et al. | 606/10 |
| 7,131,446 B2 | 11/2006 | Tang et al. | |
| 7,135,033 B2 * | 11/2006 | Altshuler et al. | 607/88 |
| 7,170,034 B2 * | 1/2007 | Shalev et al. | 219/223 |
| 7,175,950 B2 | 2/2007 | Anderson et al. | |
| 7,179,253 B2 | 2/2007 | Graham et al. | |
| 7,204,832 B2 | 4/2007 | Altshuler et al. | |
| 7,220,427 B2 | 5/2007 | Jordan | |
| 7,250,047 B2 | 7/2007 | Anderson et al. | |
| 7,253,119 B2 | 8/2007 | Dutta | |
| 7,285,364 B2 | 10/2007 | Anderson et al. | |
| 7,300,666 B2 | 11/2007 | Jordan | |
| 7,316,820 B2 | 1/2008 | Jordan | |
| 7,344,587 B2 | 3/2008 | Khan et al. | |
| 7,435,524 B2 | 10/2008 | Anderson et al. | |
| 7,468,242 B2 | 12/2008 | Bellomo et al. | |
| 7,494,493 B2 | 2/2009 | Matsuura | |
| 7,699,917 B1 | 4/2010 | Pagnotta | |
| 7,713,265 B2 | 5/2010 | Dunki-Jacobs | |
| 7,734,321 B2 | 6/2010 | White | |
| 7,834,468 B2 | 11/2010 | Dutta | |
| 7,842,029 B2 | 11/2010 | Anderson et al. | |
| 7,870,951 B1 | 1/2011 | Orsi | |
| 7,886,742 B2 | 2/2011 | Haines et al. | |
| 7,905,854 B2 | 3/2011 | Hazut et al. | |
| 7,922,688 B2 | 4/2011 | Bodduluri et al. | |
| 7,962,192 B2 | 6/2011 | Bodduluri et al. | |
| 7,967,839 B2 | 6/2011 | Flock et al. | |
| 7,985,537 B2 | 7/2011 | Zheng et al. | |
| 7,988,199 B2 | 8/2011 | Welsh | |
| 8,002,753 B2 | 8/2011 | Krumme et al. | |
| 8,036,448 B2 | 10/2011 | Gildenberg | |
| 8,088,568 B2 | 1/2012 | Bellomo et al. | |
| 8,120,485 B2 | 2/2012 | Yang | |
| 8,142,990 B2 | 3/2012 | Bellomo et al. | |
| 8,175,718 B2 | 5/2012 | Wahlgren et al. | |
| 8,182,473 B2 | 5/2012 | Altshuler et al. | |
| 8,288,347 B2 | 10/2012 | Collette et al. | |
| 8,293,463 B2 | 10/2012 | Bellomo et al. | |
| 8,303,982 B2 | 11/2012 | Smith et al. | |
| 8,317,756 B2 | 11/2012 | Krumme et al. | |
| 8,343,132 B2 | 1/2013 | Heneveld et al. | |
| 8,371,306 B2 | 2/2013 | Haines et al. | |
| 8,393,249 B2 | 3/2013 | Godoy et al. | |
| 8,394,359 B1 | 3/2013 | O'Neil | |
| 8,420,077 B2 | 4/2013 | Altman et al. | |
| 2002/0087205 A1 | 7/2002 | Chen | |
| 2002/0091377 A1 | 7/2002 | Anderson et al. | |
| 2002/0107509 A1 | 8/2002 | Neuberger et al. | |
| 2002/0123746 A1 | 9/2002 | McDaniel | |
| 2002/0128696 A1 | 9/2002 | Pearl et al. | |
| 2002/0161357 A1 | 10/2002 | Anderson et al. | |
| 2002/0173781 A1 | 11/2002 | Cense et al. | |
| 2002/0173782 A1 * | 11/2002 | Cense et al. | 606/9 |
| 2002/0193779 A1 * | 12/2002 | Yamazaki et al. | 606/9 |
| 2003/0018373 A1 | 1/2003 | Eckhardt et al. | |
| 2003/0023235 A1 | 1/2003 | Cense et al. | |
| 2003/0032950 A1 * | 2/2003 | Altshuler et al. | 606/9 |
| 2003/0036751 A1 * | 2/2003 | Anderson et al. | 606/9 |
| 2003/0060810 A1 | 3/2003 | Syrowicz et al. | |
| 2003/0113540 A1 | 6/2003 | Anderson et al. | |
| 2003/0159615 A1 | 8/2003 | Anderson et al. | |
| 2003/0175116 A1 | 9/2003 | Le Biez et al. | |
| 2003/0184831 A1 | 10/2003 | Lieberman | |
| 2004/0015156 A1 | 1/2004 | Vasily | |
| 2004/0133251 A1 | 7/2004 | Altshuler et al. | |
| 2004/0228818 A1 | 11/2004 | Simon et al. | |
| 2005/0137584 A1 | 6/2005 | Lemchen | |
| 2005/0143719 A1 | 6/2005 | Sink | |
| 2005/0234527 A1 | 10/2005 | Slatkine | |
| 2005/0234528 A1 | 10/2005 | Tang et al. | |
| 2005/0278002 A1 | 12/2005 | Eimerl et al. | |
| 2006/0020260 A1 | 1/2006 | Dover et al. | |
| 2006/0047330 A1 | 3/2006 | Whatcott et al. | |
| 2006/0165657 A1 | 7/2006 | Bernasconi et al. | |
| 2006/0178659 A1 | 8/2006 | Van Hal et al. | |
| 2006/0206173 A1 | 9/2006 | Gertner et al. | |
| 2006/0207978 A1 | 9/2006 | Rizun et al. | |
| 2006/0276859 A1 | 12/2006 | Ferren et al. | |
| 2006/0276860 A1 | 12/2006 | Ferren et al. | |
| 2007/0027440 A1 | 2/2007 | Altshuler et al. | |
| 2007/0032846 A1 | 2/2007 | Ferren et al. | |
| 2007/0118098 A1 | 5/2007 | Tankovich | |
| 2007/0160958 A1 | 7/2007 | Belikov et al. | |
| 2007/0213791 A1 | 9/2007 | Van Hal et al. | |
| 2008/0039827 A1 | 2/2008 | Ferren et al. | |

(56) References Cited

U.S. PATENT DOCUMENTS

| | | |
|---|---|---|
| 2008/0145326 A1 | 6/2008 | Ferren et al. |
| 2008/0269575 A1 | 10/2008 | Iddan |
| 2009/0076622 A1 | 3/2009 | Thompson et al. |

OTHER PUBLICATIONS

Hunter, Ian W.; Brenan, Colin J.H.; Sebern, Elizabeth L.; Design and Characterization of a Laser-based Instrument to Treat Hemangiomas Using Spectroscopic Feedback: The "Smart Scalpel"; MIT Home Automation and Healthcare Consortium; bearing a date of Oct. 1, 1999; Progress Report No. 2-4; pp. 1-16.
Keis, Karin; Kamath, Yash K; "Objective Measurement of Hair Lustre"; Business Briefing: Global Cosmetics Manufacturing; bearing a date of 2004; pp. 1-5.
Lach, Elliot M.D.; "Dermatology and Plastic Surgery"; pp. 126-133; located at: Absten, Gregory T., BSc, MBA; "Laser Medicine and Surgery"; bearing dates of 1996, 1999 and 2000; pp. 1-2; located at: http://www.lasertraining.org/fundamen.htm; printed on Nov. 4, 2004.
Ley, Brian; "Diameter of a Human Hair"; The Physics Factbook; bearing a date of 1999; p. 1 of 1; located at: http://hypertextbook.com/facts/1999/BrianLey.shtml; printed on Jan. 17, 2005.
Marschner, Stephen R.; Jensen, Henrik Wann; Cammarano, Mike; Worley, Steve; Hanrahan, Pat; "Light Scattering from Human Hair Fibers"; pp. 1-12.
"More About Laser Hair Removal"; ShoreLaser center; bearing a date of Feb. 23, 2004; pp. 1-8; located at: http://www.shorelaser.com/LaserHairDet.html; printed on Jan. 21, 2005.
Owens, Shelby, CME; "Photobiology of the Skin"; consumerbeware.com; bearing dates of 1998-2002; pp. 1-7; located at: http://www.consumerbeware.com/integumen2.htm; printed on Oct. 6, 2004.
Owens, Shelby, CME; "Photobiology of the Skin"; consumerbeware.com; bearing a dates of 1998-2002; pp. 1-4; located at: http://www.consumerbeware.com/integumen.htm; printed on Oct. 11, 2004.
Pope, Karl; "Comparative Monte Carlo Examination of Energy Penetration for Different Hair Removal Lasers"; Clinical Update; Jan. 2000; pp. 1-4; Candela Corporation; Wayland, Massachusetts; USA.
Sobottka, Gerrit; Weber, Andreas; "Übersicht über die optischen Eigenschaften von Human-Haar"; Computer Graphics Technical Reports, CG-2002/1; bearing a date of Apr. 12, 2002; pp. 1-8; Institut für Informatik II, Universität Bonn; Bonn, Germany.
Stamm, Robert F.; Garcia, Mario L.; Fuchs, Judith J.; "The optical properties of human hair I. Fundamental considerations and goniophotometer curves"; Journal of the Society of Cosmetic Chemists; bearing dates of Nov. 17, 1976, Sep. 1977; vol. 28, No. 9; pp. 571-599; The Society of Cosmetic Chemists, Inc.
Ward, Kelly; Galoppo, Nico; Lin, Ming C.; "Modeling Hair Influenced by Water and Styling Products"; pp. 1-8; University of North Carolina at Chapel Hill.
Springen, Karen; "Hair Today, Gone Tomorrow"; MSNBC.com; Jul. 12, 2005; pp. 1-3; Newsweek, Inc.; located at http://www.msnbc.msn.com/id/8543585/site/newsweek/; printed on Jul. 15, 2005.
U.S. Appl. No. 11/217,111, Ferren et al.
U.S. Appl. No. 11/198,910, Ferren et al.
U.S. Appl. No. 11/175,984, Ferren et al.
U.S. Appl. No. 11/171,649, Ferren et al.
U.S. Appl. No. 11/143,925, Ferren et al.
U.S. Appl. No. 11/143,116, Ferren et al.
U.S. Appl. No. 11/072,698, Ferren et al.
U.S. Appl. No. 11/072,007, Ferren et al.
'Nano-tattoo' May Help Diabetics Track Their Blood Sugar; Chemistry/Analytical Chemistry; May 28, 2010; 2 pages; located at www.physorg.com/news194248207.html.
"Photoepilation: A comparative analysis of different light sources for better epilation efficacy"; pp. 1-7; located at: http://www.solarlaser.com/photoepilation_1_en.htm; printed on Oct. 6, 2004.
Bozkurt, Alper; Onaral, Banu; "Safety assessment of near infrared light emitting diodes for diffuse optical measurements"; BioMedical Engineering OnLine; bearing dates of Oct. 6, 2004, Jan. 30, 2004, Mar. 22, 2004, 1999-2004; pp. 1-11; located at: http://www.biomedical-engineering-online.com/content/3/1/9; BioMed Central; printed on Oct. 6, 2004.
Dierickx, Christine C., M.D.; "Laser Hair Removal: Scientific Principles and Practical Aspects"; bearing a date of 2002; pp. 1-8.
Marschner et al.; "Light Scattering from Human Hair Fibers"; ACM Transactions on Graphics (TOG); published on Jul. 27, 2003; pp. 780-791 plus 2 cover sheets; vol. 22, Issue 3; ACM.
Ward et al.; "Modeling Hair Influenced by Water and Styling Products"; International Conference on Computer Animation and Social Agents (CASA); bearing a date of 2004; pp. 207-214 plus cover sheet.

\* cited by examiner (SIDE VIEW)　　　　　　　　(END VIEW)

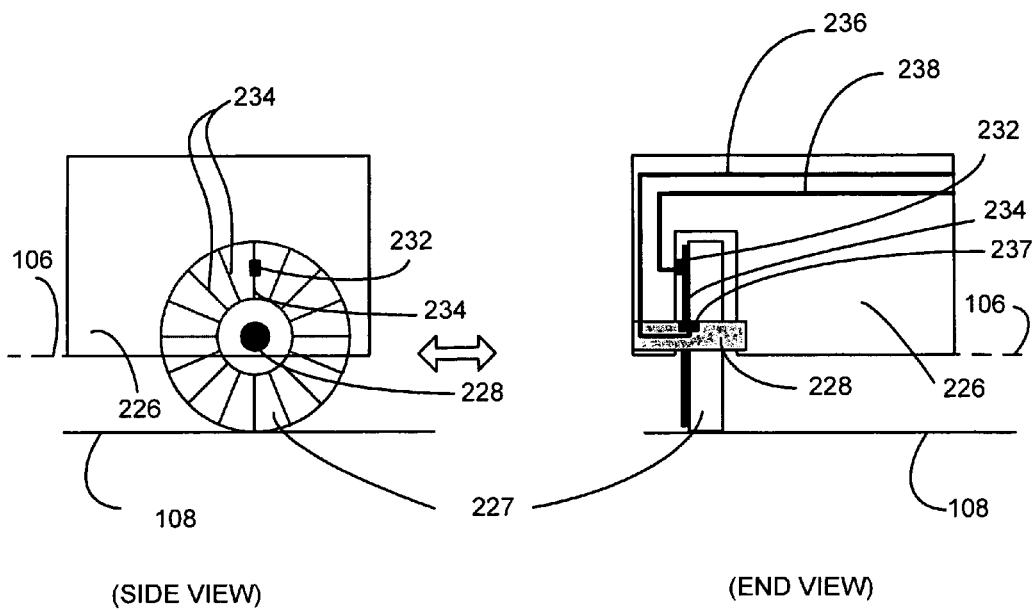
(SIDE VIEW)      (END VIEW)
FIG. 9A      FIG. 9B
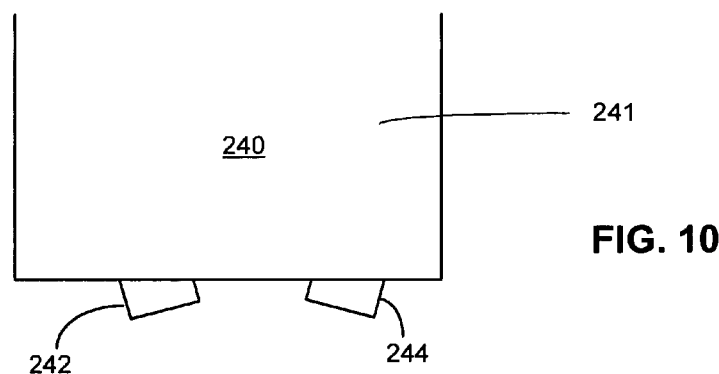
FIG. 10

METHOD AND SYSTEM FOR TEMPORARY HAIR REMOVAL

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s); the present application also claims the earliest available effective filing date(s) from, and also incorporates by reference in its entirety all subject matter of any and all parent, grandparent, great-grandparent, etc. applications of the following listed application(s):

1. United States patent application entitled HAIR TREATMENT SYSTEM, naming Bran Ferren, Muriel Y. Ishikawa, Edward K. Y. Jung, Nathan P. Myhrvold, Clarence T. Tegreene and Lowell L. Wood, Jr. as inventors, filed substantially contemporaneously herewith.
2. United States patent application entitled HAIR REMOVAL SYSTEM WITH LIGHT SOURCE ARRAY, naming Bran Ferren, Muriel Y. Ishikawa, Edward K. Y. Jung, Nathan P. Myhrvold, Clarence T. Tegreene and Lowell L. Wood, Jr. as inventors, filed substantially contemporaneously herewith.

TECHNICAL FIELD

The present application relates, in general, to the field of hair treatment devices and methods, and more particularly to depilation devices and methods.

SUMMARY

Embodiments of methods and systems for removal or modification of hair using electromagnetic energy are described. Features of various embodiments will be apparent from the following detailed description and associated drawings.

BRIEF DESCRIPTION OF THE FIGURES

Features of the invention are set forth in the appended claims. The exemplary embodiments may best be understood by making reference to the following description taken in conjunction with the accompanying drawings. In the figures, like referenced numerals identify like elements.

FIGS. 9A and 9B illustrate mechanical-electrical motion sensor;
FIG. 10 illustrates an optical motion sensor.

DETAILED DESCRIPTION

In the following detailed description, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context dictates otherwise. The meaning of "a", "an", and "the" include plural references. The meaning of "in" includes "in" and "on." A reference to the singular includes a reference to the plural unless otherwise stated or inconsistent with the disclosure herein.

Figure 1:
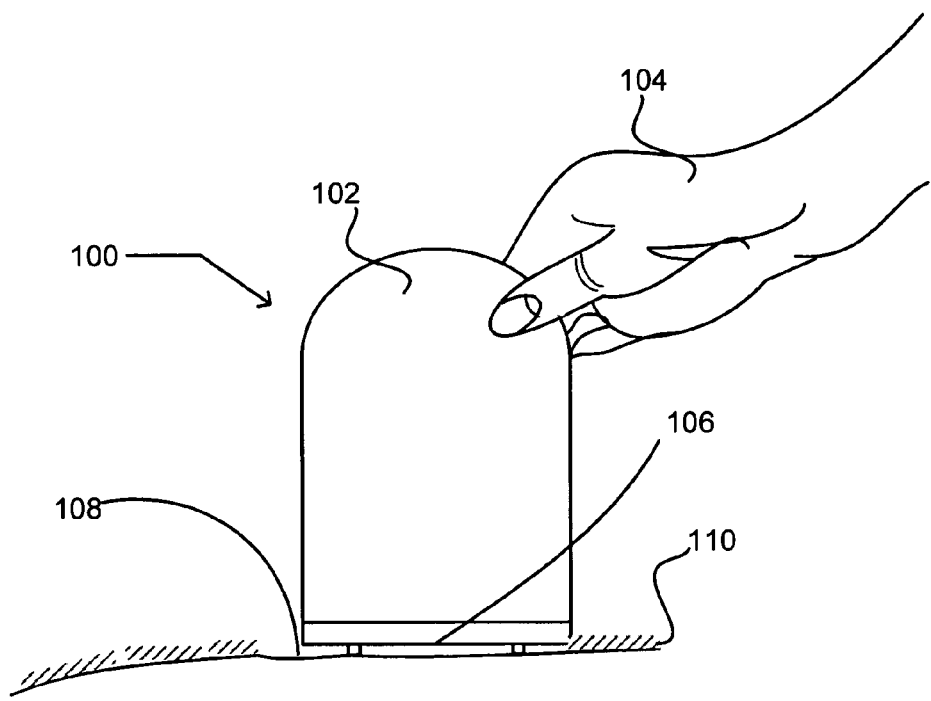
FIG. 1 depicts the use of an exemplary embodiment.

FIG. 1 illustrates the use of an exemplary embodiment of a depilation device 100. Device 100 of FIG. 1 includes a housing 102 which is of a size and shape suitable for being held in the hand 104 of a user. Certain components of the device 100 are housed within the housing 102. The device 100 includes an active surface 106 which is placed against a skin surface 108 on which are hairs 110 that are to be shaved or trimmed.

Figure 2:
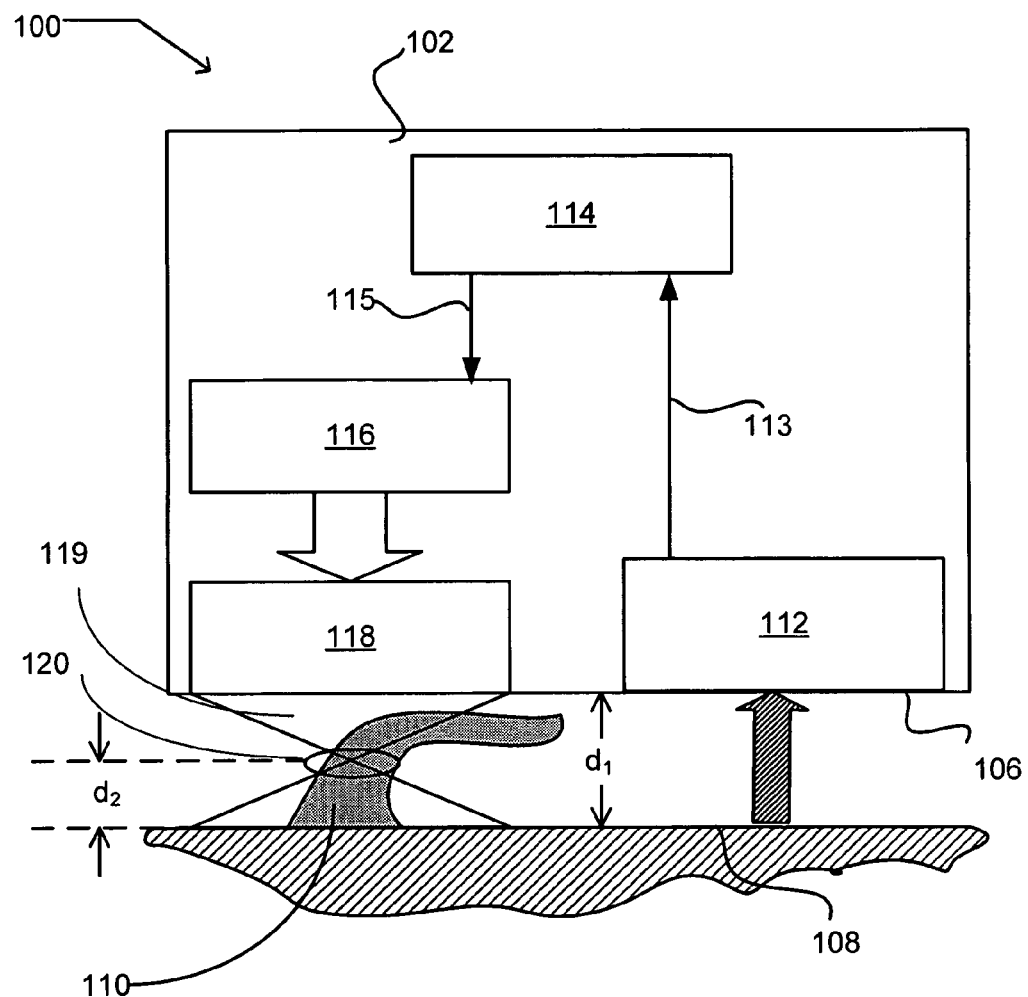
FIG. 2 is a block diagram of an embodiment of a depilation device.

FIG. 2 is a schematic diagram of a depilation device 100 of the type illustrated in FIG. 1. Depilation device 100 includes housing 102 and active surface 106. Located within housing 102 are a proximity sensor 112, control circuitry 114, light source 116, and a high numerical aperture lens 118. Proximity sensor 112 detects proximity of active surface 106 to the skin surface 108 and transmits proximity sense signal 113 to control circuitry 114. High numerical aperture lens 118 modifies a beam of light from light source 116 to form a beam which converges to a narrow beam waist 120 and subsequently diverges.

In use, depilation device 100 is positioned over skin surface 108 with active surface 106 adjacent skin surface 108. When the active surface 106 of depilation device 100 is positioned at a distance $d_1$ from skin surface 108, beam waist 120 is located at a distance $d_2$ from skin surface 108. At this distance, a hair 110 located in the beam may be severed at beam waist 120, while the beam will have diverged before reaching the skin surface to reduce the possibility of damage or irritation of the skin. For this and other embodiments, the position at which the hair shaft is severed may be selected to produce a desired effect; e.g., for a "close shave", as may be desired for hair on the face, legs, etc., $d_2$ may be in the range of a few microns, dimensions on the order of one or a few hair diameters, or other appropriate ranges as may for example trim the hair substantially at the skin surface without being close enough to irritate or damage the skin. Hair may be trimmed further from or closer to the skin surface, as desired, by modifying $d_2$, and such configurations are also considered to fall within the scope of the invention.

In addition to modifying the distance between active surface 106 and skin surface 108, in some embodiments the position of beam waist 120 may be adjusted with respect to skin surface 108, at least within a limited range, by adjusting the position of one or both of light source 116 and lens 118 with respect to active surface 106.

An embodiment of a depilation method may include detecting proximity of a depilation device to a skin surface, responsive to detecting proximity of the depilation device to skin surface delivering a beam of highly convergent light from the depilation device to the skin surface, and delivering the light for a duration and with an intensity sufficient to sever at least one hair shaft. The beam of light may have a beam waist positioned substantially at the base of at least one hair shaft. Detecting proximity of the depilation device to the skin surface may include determining that the depilation device is within a predetermined distance range of the skin surface. The depilation device may include a light source, which in some embodiments may be enclosed within the depilation device. Alternatively, the light source may be located remote from the depilation device, with the depilation device receiving light from the remote light source via an optical coupling. In most embodiments the duration and the intensity of the light at the skin surface will be controlled so that they are insufficient to cause skin damage or irritation. The light may be delivered as a single pulse or a series of pulses. Pulse duration may be selected based upon one or more parameters of a hair shaft on which it is focused, e.g. light absorption spectrum, shaft dimension, etc. The device may be operable within a range of distances of the skin surface. Proximity or position sensing may be used to detect that the device is within the specified distance range, and permitting the device to be activated manually by the user (e.g. with a switch) when it is within the specified distance range.

In some embodiments, the depilation device may include a light source, a lens, a proximity sensor, and control circuitry. The light source may be capable of producing light of a wavelength band absorbed by hair. The lens may be positioned to receive light from the light source and configured to form a highly convergent beam having a narrow spatially limited beam waist from the received light. The proximity sensor may be capable of detecting proximity of the light source to a skin surface and generating a proximity sense signal indicative of the proximity. The control circuitry is configured to gate the light in response to the proximity sense signal. The detected proximity may correspond to a selected distance range of the light source from the skin surface.

In certain embodiments the beam of light may have an angle of convergence of between about 30 and about 80 degrees relative to the axis of the beam. In other embodiments, angles of convergence of between about 40 and about 60 degrees may be used. In still other embodiments, angles of convergence between about 45 and about 55 degrees relative to the axis of the beam may be used. Delivering a beam of highly convergent light may include the step of focusing a beam of light. It may also include forming a short narrow beam waist. The term short beam waist, as used herein, includes beam waists in the range of about 1 µm to about 100 µm, and more specifically, in the range of about 5 µm to about 30 µm. The diameter of the beam at the skin surface may be between about two and about ten times the diameter of the beam at the beam waist. In some embodiments, the diameter of the beam at the skin surface may be between about two and three times the diameter of the beam waist. The intensity of the beam of light at the skin surface may be between about one fourth and about one ninth the intensity of the beam at the beam waist. In other embodiments the intensity of the beam at the skin surface may between about one fourth and one hundredth of the intensity of the beam at the beam waist. The duration and intensity of the light may be sufficient to cause absorption of light by the hair shaft, at the beam waist, of between about 50 and about 200 joules per gram. In other embodiments the duration and intensity of the light may be sufficient to cause absorption of between about 50 and about 100 joules per gram of energy from the light by the hair shaft at the beam waist. In most cases the absorption of light by the hair shaft will preferably be sufficient to cause mechanical damage or disruption of the hair shaft, while the light absorption at the skin surface will preferably be in a range that does not cause irritation or damage to the skin. In some embodiments, the duration and intensity of the light may be sufficient to cause absorption of between about 20 and about 40 joules per gram of energy from the light by the skin surface. In still other embodiments the duration and intensity of the light may be sufficient to cause absorption of between about 10 and about 80 joules per gram of energy from the light by the skin surface. The light fluence at the beam waist may be between about 4 and about 100 times the light fluence at the skin surface, or, in some embodiments, the light fluence at the beam waist is between about four and about nine times the light fluence at the skin surface. Light fluence levels below the level that causes mechanical damage or severing of the hair shaft may produce bleaching of the hair shaft.

In some embodiments, the beam waist may be positioned between about 1 and about 3 hair diameters above the skin surface. In other embodiments, the beam waist diameter may be between about 1 and about 3 hair diameters. In some embodiments, the beam waist may be positioned between about 40 µm and about 300 µm above the skin surface. In most embodiments, the beam waist diameter may be between about 17 µm and about 600 µm; in some embodiments, the beam waist diameter may be between about 30 µm and about 300 µm, while in some embodiments it may be between about 50 µm and about 100 µm.

As described previously, the lens may be a high numerical aperture lens. The lens may have a numerical aperture of between about 0.5 and about 0.98. In certain embodiments, the lens may have a numerical aperture of between about 0.64 and about 0.87. In some embodiments, the lens may have a numerical aperture of between about 0.71 and 0.83. In some embodiments, the lens may have an f-number of between about 1.2 and about 11.3. In some embodiments, the lens may have an f-number of between about 1.68 and about 3.46, and in some embodiments, the lens may have an f-number of between about 2 and about 2.86.

Figure 3:
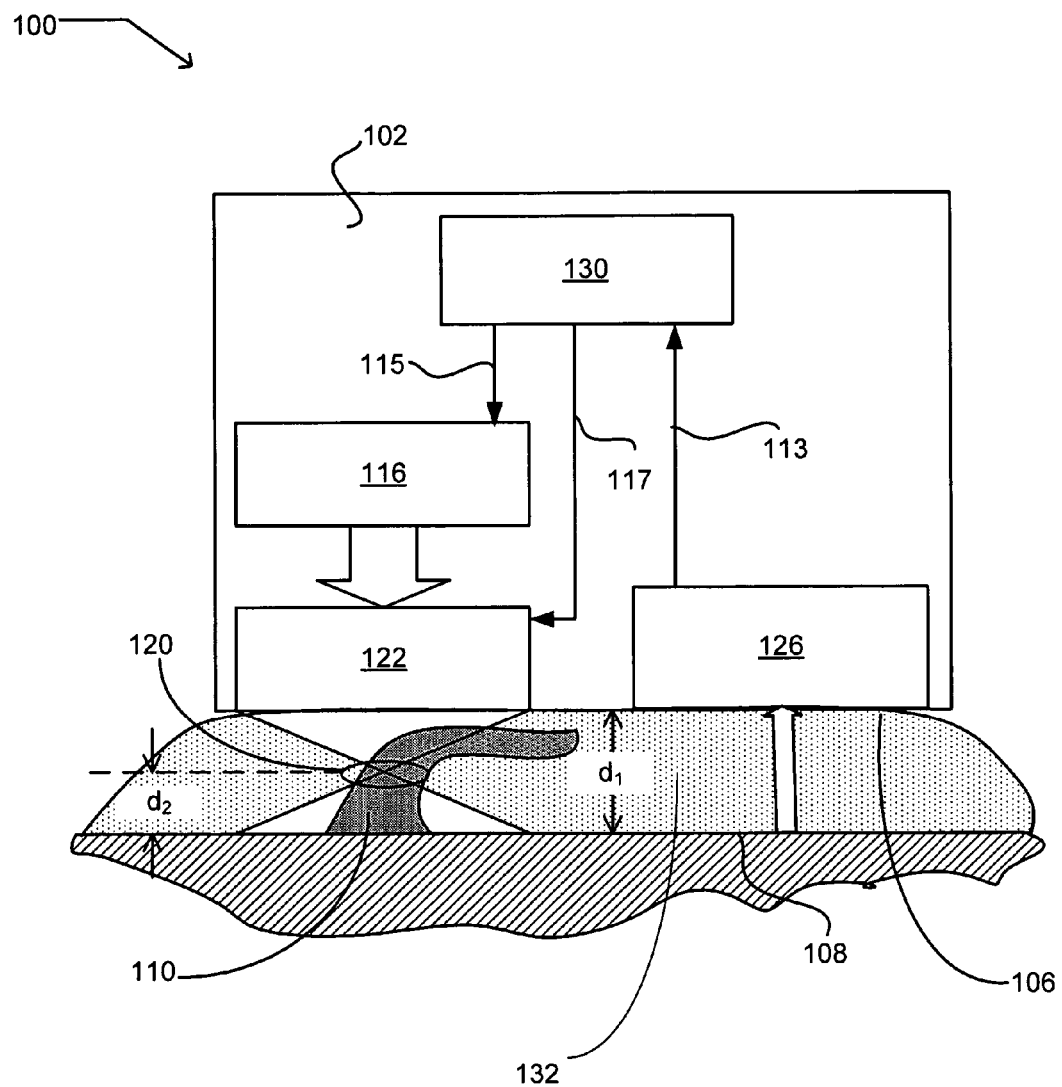
FIG. 3 is a block diagram of a further embodiment of a depilation device.

Beam performance can be modified, e.g., to obtain a larger angle of optical convergence, by disposing a medium 132 with an index of refraction different than that of air between skin surface 108 and active surface 106 of depilation device 100, as depicted in FIG. 3. Medium 132 may be, for example, oil, glycerin, alcohol, or various other substances that are substantially transparent to the frequency of optical radiation being employed. Medium 132 may be a liquid, gel, or gas. In further alternative embodiments, medium 132 may act in various other ways to modulate the effect of light from light source 116. Medium 132 may include light activated chemicals such as a bleaching agent, colorant, dye, conditioner, etc., and may cause light to have an effect on hair different from or in addition to cutting or producing mechanical damage to hair. Medium 132 may contain light absorbing or reflecting materials, and in some embodiments may function to protect the skin surface from damaging effects of light. Although in FIG. 3 medium 132 fills substantially the entire space between skin surface 108 and active surface 106, in other embodiments the medium may fill only a portion of the space, coating the skin surface or coating individual hair shafts.

FIG. 3 depicts an embodiment of the device depicted in FIG. 2, in which photodetector 126 functions as a proximity sensor. A system for treating skin according to one embodiment may include a housing, at least one light source carried by the housing and capable of producing light of a waveband absorbed to a useful degree by hair, an optical system configured to modify light from the light source to produce a highly convergent beam having a beam waist, at least one photo detector adapted to detect light from the skin structure, and a controller responsive to detection of light by the photo detector. The photo detector is positioned in the housing relative to the light source so that the photo detector is oriented to detect light from the skin structure when the light source is positioned within a selected distance range of the skin structure. The controller is configured to control delivery of light such that the beam waist is positioned at a known position with respect to the skin structure when the light source is within the selected distance range. The system may also include one or more of a laser drive circuit, a power supply, and/or a secondary illumination source.

While the optical system is presented as including a high numerical aperture lens, the optical system may include additional elements in some applications. In the single lens case or other configurations, the optical system may have an output numerical aperture of between about 0.5 and about 0.98. In some embodiments, the numerical aperture of the optical system may be between about 0.64 and about 0.87. In some embodiments, the numerical aperture of the optical system may be between the about 0.71 and about 0.82. The optical system may have an f-number of between about 1.2 and about 11.3. In another embodiment the optical system may have an f-number of between about 1.68 and about 3.46. In still another embodiment, the optical system may have an f-number of between about 2 and about 2.86. As an example of additional elements that may be appropriate in some configurations, the optical system may include a beam expander interposed between the light source and the high numerical aperture lens. The optical system may include one or more adjustable lenses or other adjustable optical elements, which may be controlled by a controller, such as controller 130, which sends control signals 117 to optical system 122. Optical system 122 may include one or more actuation mechanisms for controlling positions or settings of optical elements, including, but not limited to, adjustable lenses, By adjusting the position, angle, or lens strength (zoom) of one or more optical components, the position of the beam and beam waist can be adjusted with respect to height (distance from the skin surface) or X-Y position (i.e., position in a plane parallel to the skin surface).

Such adjustments may take into account the distance of the device 100 with respect to the skin surface, and optical system components may be moved with respect to other portions of device 100, to obtain correct positioning of the beam waist relative to the skin surface.

Light reflected or emitted from skin surface 108 in response to delivery of light to skin surface 108 from light source 116 is detected by photo detector 126 when active surface 106 of depilation device 100 is within a selected distance range of skin surface 108. Proximity sense signal 113 is delivered to controller 130 in FIG. 3, which provides comparable functionality to control circuitry 114 shown in FIG. 2. Controller 130 may include at least one of analog circuitry, digital circuitry, and a microprocessor. If proximity sense signal 113 indicates that active surface 106 is within the selected distance range of skin surface 108, control signal 115 is generated to control light source 116 to generate light. Light from light source 116 is modulated by optical system 118 to generate beam 119 having beam waist 120 located at a distance $d_2$ above skin surface 108.

The light source may be activatable to produce light only when the depilation device is within the pre-determined distance range of the skin surface. Various mechanisms may be used to gate either the production or delivery of light. Light may be produced by the light source at other times as well, but may be delivered to the skin surface only when the depilation device is within the predetermined distance range of the skin surface. This may be accomplished, for example, by blocking delivery of light to the skin surface by a shuttering or beam-interdiction mechanism when the depilation device is not within the predetermined distance range of the skin surface.

In embodiments in which a close shave is desired, the distance range between the active surface (or other landmark on the depilation device) and the skin surface may be selected to position the beam waist just above the skin surface.

In the various embodiments, including but not limited to those depicted and described herein, various light sources may be used. In general, such light sources will be sources of focusable optical power. Light sources may have wavelength bands including one or more wavelengths absorbed by hair. Specifically, in most embodiments, a light source with a free-space wavelength or frequency band that is or includes one or more wavelengths or frequencies absorbed significantly by hair. Wavelengths or frequencies that are absorbed preferentially by hair in comparison to skin may be used. Light sources include, but are not limited to, lasers, laser diodes, and light emitting diodes. The light source may be a near-infrared source, such as a Nd (neodymium):YAG laser. Alternatively, the light source may be an IR laser. The light source may be of a type that emits light having a free-space wavelength between about 0.8 µm and about 1.7 µm. If multiple light sources are used, they may include combinations of light sources of different types.

Figure 4:
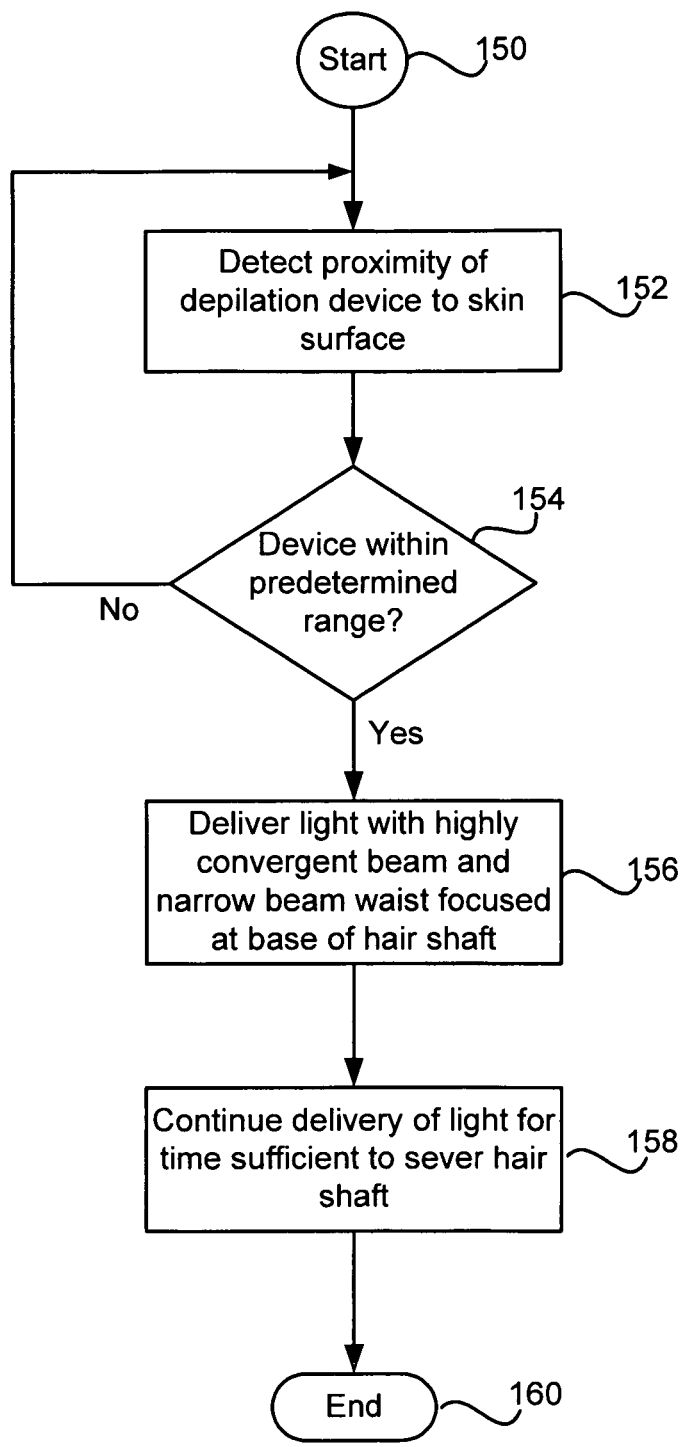
FIG. 4 is a flow diagram of an exemplary depilation method.

FIG. 4 is a flow diagram depicting selected steps of operation of the embodiments of FIGS. 2 and 3. At step 152, proximity of the depilation device to the skin surface is detected. If the device is not within a predetermined range, as determined at step 154, process control returns to step 152, and the proximity of the depilation device to the skin surface is again detected. This step is repeated until the device is within the predetermined range. If at step 154 the device is found to be within the predetermined range, process control moves to step 156, and light with a highly convergent beam and a narrow beam waist focused at the base of a hair shaft is delivered to a hair shaft that's within optical range of the device's optical system. At step 158, delivery of light is continued for a time sufficient to sever the hair shaft.

Generating a convergent beam may include passing light from the light source through a high numerical aperture lens. In some cases, generating the convergent beam may include defocusing light from a laser source prior to passing the light through a high numerical aperture lens. In many applications, it is preferred that the convergent beam have a duration and intensity that is sufficient to cause mechanical failure of the hair shaft at the beam waist, but insufficient to cause skin damage or irritation of the skin surface.

In another embodiment, a method is provided for depilating the skin surface that includes positioning a laser source activatable to produce a highly convergent beam substantially adjacent the skin surface, determining the distance of the laser source from the skin surface, and, if the determined distance is within a specified range, activating the laser source to generate the highly convergent beam for a duration and with an intensity sufficient to cause mechanical failure of a hair shaft growing from the skin surface. The method may include the step of detecting the presence of a hair shaft on the skin surface and activating the laser source to generate a highly convergent beam with a narrow beam waist located at the base of hair shaft.

Figure 5:
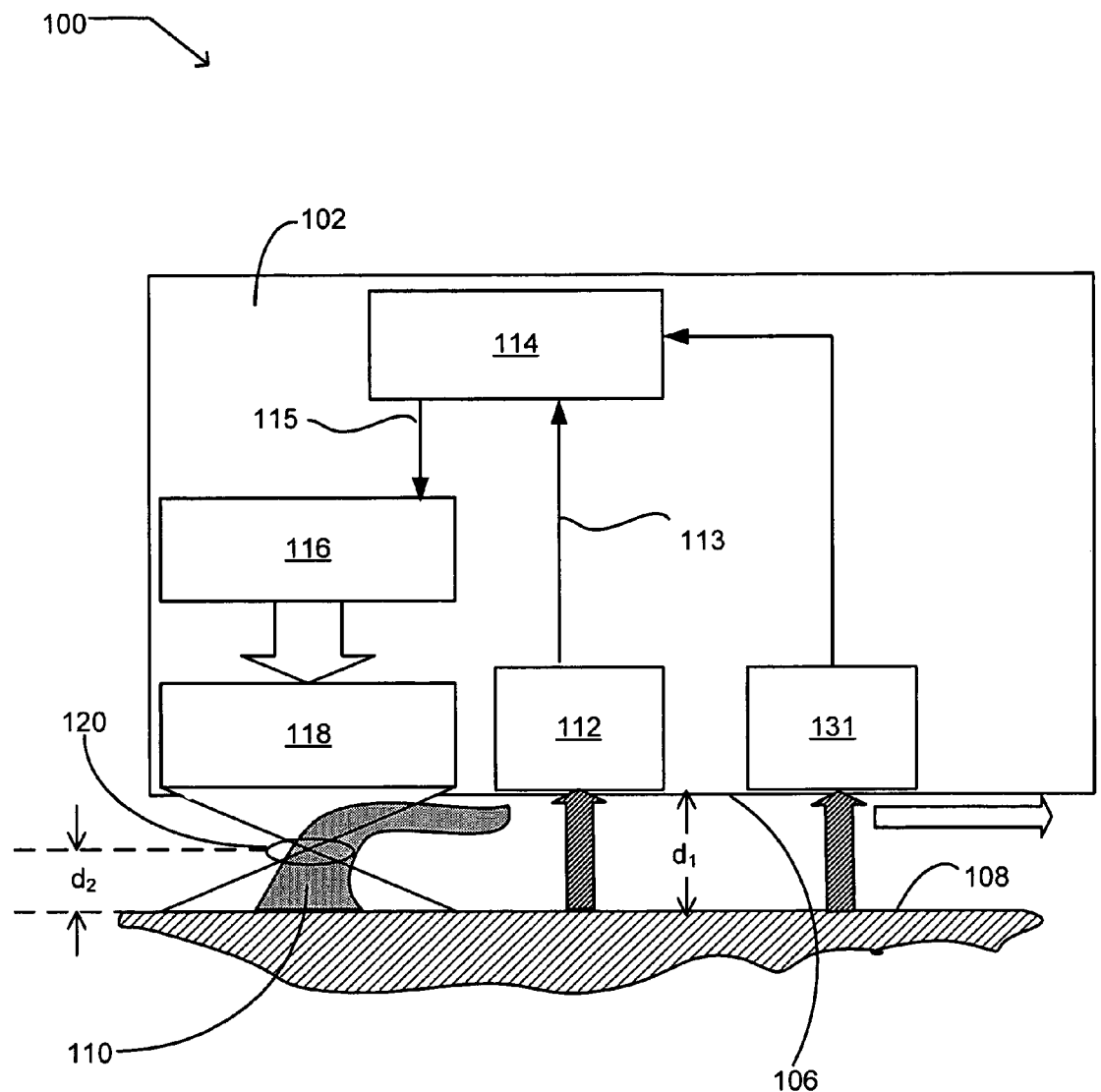
FIG. 5 is a block diagram of an embodiment of a depilation device including motion sensing.

FIG. 5 illustrates a further embodiment of depilation device 100. Depilation device 100 includes proximity sensor 112, light source 116, high numerical aperture lens 118, motion sensor 131, and control circuitry 114. These components are housed within housing 102. Light from light source 116 is focused by high numerical aperture lens 118 to form a beam which converges to a narrow beam waist 120, and subsequently diverges. When active surface 106 of depilation device 100 is positioned at a distance $d_1$ above skin surface 108, as detected by proximity sensor 112, beam waist 120 is positioned at a distance $d_2$ above skin surface 108. Motion of depilation device 100 across skin surface 108 is detected by motion sensor 131.

Figure 6:
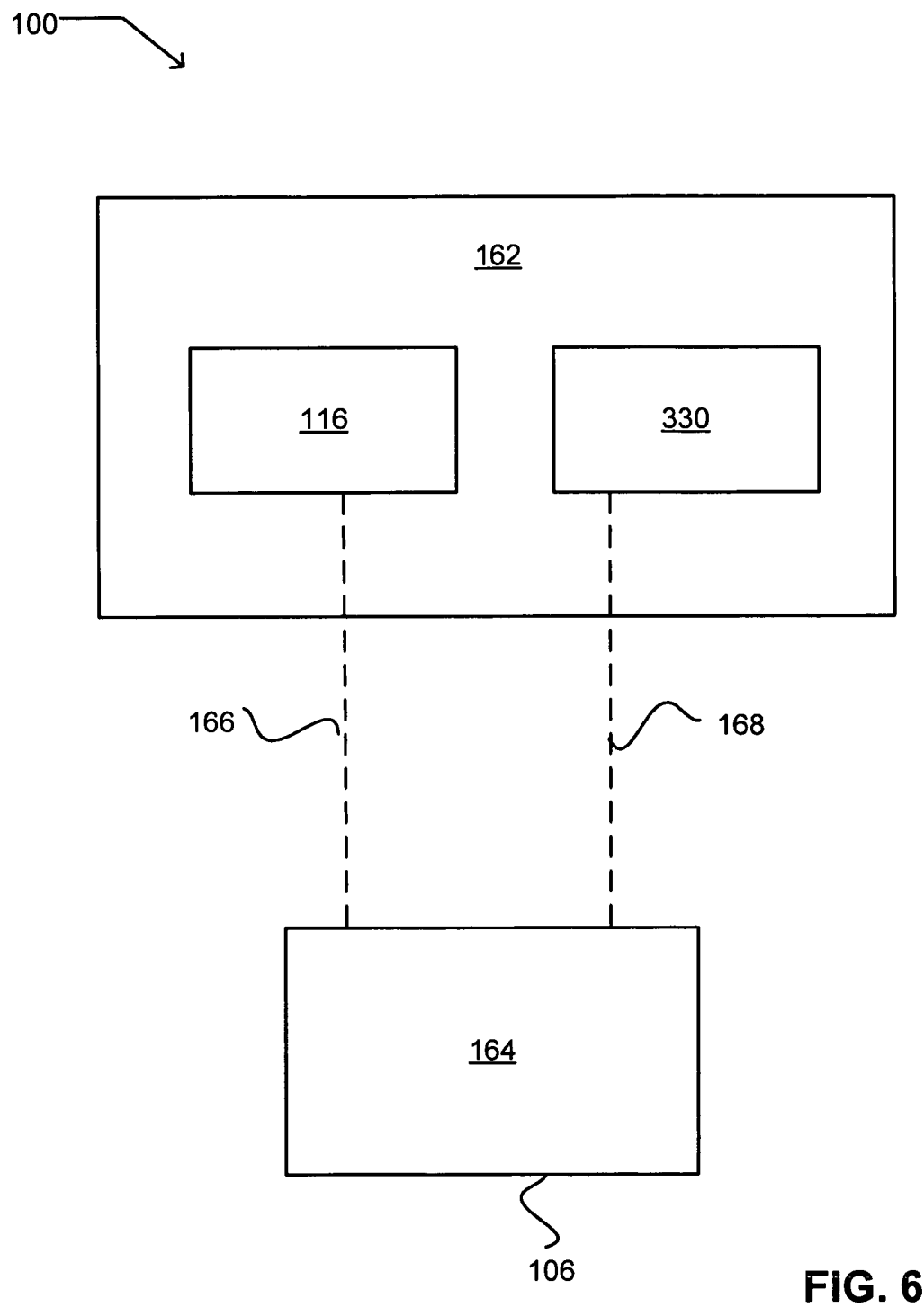
FIG. 6 illustrates an embodiment including a base unit and a handset.

As illustrated in FIG. 6, the depilation device may include a handset 164 and base unit 162. Handset 164 may include a high numerical aperture lens and a proximity sensor, and have an active surface 106. Base unit 162 may contain light source 116 and power source 330. Optical link 166 and power link 168 between base unit 162 and handset 164 may be configured to transmit light from light source 116 and power from power source 330 to handset 164. In some embodiments control circuitry may be located in the handset. In some embodiments control circuitry may be located in the base unit and control signals transmitted to the handset by one of electrical connection, an optical connection, or a wireless connection. The control circuitry may include at least one of analog circuitry, digital circuitry, and a microprocessor. The control circuitry may be located in a base unit, and data transmitted between the handset and the base unit by one of an electrical connection, an optical connection, or a wireless connection. Alternatively, control circuitry may be located in the handset. Distribution of system components between base unit 162 and handset 164 may be designed so that bulky and/or heavy system components are located in base unit 162, so that handset 164 is convenient to use.

Figure 7A:
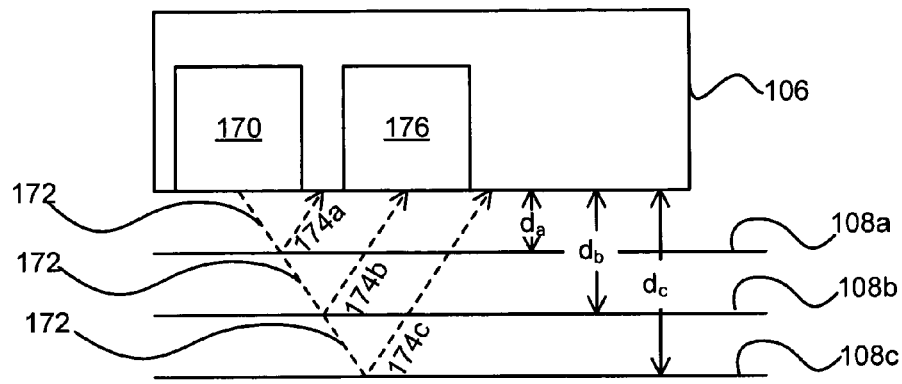
FIG. 7A illustrates an optical proximity sensor.
Figure 7B:
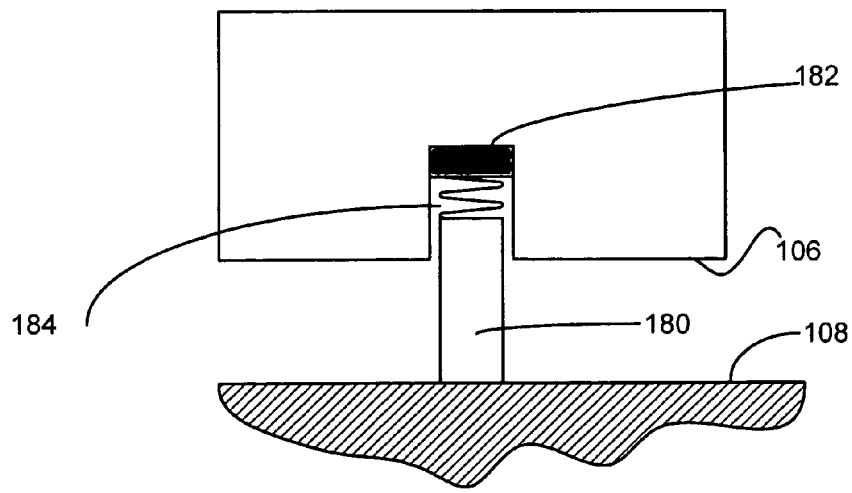
FIG. 7B illustrates a mechanical proximity sensor.
Figure 7C:
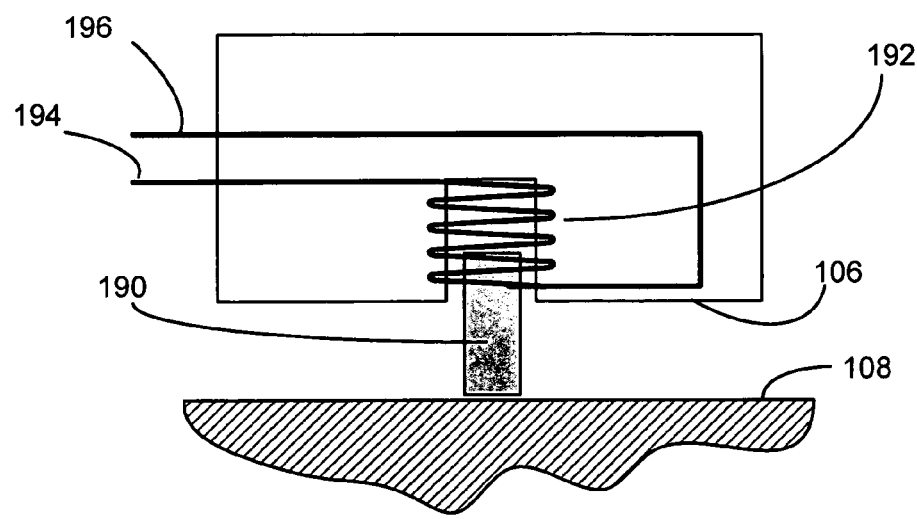
FIG. 7C illustrates an electromechanical proximity sensor.

FIGS. 7A-7C depict exemplary proximity sensors that may be used in the practice of the invention. FIG. 7A depicts an optical proximity sensor that includes light source 170 and light detector 176. Light source 170 generates a beam 172, which is reflected off of the skin surface. When the proximity sensor is located at a distance $d_a$ from the skin surface (indicated by reference number 108a), the reflected beam 174a returns to active surface 106 at a location between light source 170 and light detector 176, so reflected beam 174a is not detected by light detector 176. When the proximity sensor is located at a distance $d_b$ from the skin surface (indicated by reference number 108b), the reflected beam 174b returns to active surface 106 at light detector 176, where it may be detected. When the proximity sensor is located at a distance $d_c$ from the skin surface (indicated by reference number 108c), the reflected beam 174c returns to active surface 106 at a location beyond light detector 176, where reflected beam 174c is not detected by light detector 176. By adjusting the relative positions and orientations of light source 170 and light detector 176, the distance between the skin surface and proximity sensor at which reflected beam 174 is detected may be selected. $d_b$, the distance at which the reflected beam may be detected, thus represents a preferred distance of the proximity sensor from the skin surface.

In some embodiments, removing hair from the skin may include positioning a hair removal device adjacent the skin surface, detecting a distance of an active surface of the hair removal device from the skin surface, detecting the presence of at least one hair shaft on the skin surface adjacent the active surface, and if the active surface of the hair removal device is within a specified distance range of the skin surface and at least one hair shaft is detected, activating a laser source to generate a convergent beam having a beam waist positioned substantially coincident with a base of the hair shaft. In one embodiment, detecting the distance of the hair removal device from the skin surface includes detecting an optical signal from the skin surface. The detected optical signal may originate from the laser source and be reflected from the skin surface, or the detected optical signal may be light originating from a secondary light source reflected from the skin surface. Moreover, detected light may not simply be reflected from the skin surface, but may include light that has entered the skin surface, and been diffused, diffracted, scattered or modified in some other manner before exiting the skin surface and being detected by the detector. In some cases the detected optical signal may not be light that is reflected from the skin surface, but rather light that is emitted from the skin surface in response to illumination by a secondary light source.

In the embodiment of FIG. 7A, the light detector may simply include a single photodetector. Detection may be based on one or both of light intensity and location. More complex detection systems including multiple photodetectors may also be used. In some embodiments, CCD or CMOS image sensors may be used to detect an image of the spot formed by the beam on the skin surface, and the detected spot used as an indication of the distance of the device from the skin surface, because the spot becomes smaller and more intense as the beam waist approaches the skin surface.

Various configurations of light sources and sensors may be devised; depending on configuration, the output of the sensor may indicate various parameters, including distance of various portions of the depilation device from the skin. Some sensors may provide a distance measure, while others may simply indicate whether or not the device is within a specified distance or distance range of the skin. Distance or proximity sensing is not limited to optical sensing. Detecting proximity of the depilation device to the skin surface may before performed with one or more of an optical sensor, a mechanical sensor, an electromechanical sensor, an acoustic sensor, a capacitive sensor, or various other distance or proximity measuring devices and systems which are known or may be developed by those of skill in the art.

FIG. 7B illustrates a proximity sensor based on a rigid probe 180 linked to a pressure transducer 182 by a spring 184. The signal generated by the pressure transducer may vary as a function of the distance between probe 180 and skin surface 108, between the distance at which probe 180 contacts skin surface 108 and the distance at which spring 184 is fully compressed. At either end of the selected distance range, the sensor output will be substantially constant.

FIG. 7C illustrates a proximity sensor based on an inductor coil 192 connected to leads 194 and 196, which may be connected to additional electronic circuitry (not shown). Rod 190 is positioned within inductor coil 192, and as rod 190 contacts skin surface 108 and is pushed further into coil 192, the impedance of coil 192 changes and can be detected electrically to provide an indication of the distance to which the rod penetrates the coil 192. While the exemplary embodiment of FIG. 7C depicts an inductive proximity sensor, a variety of other approaches to proximity sensors may be implemented according to known techniques. For example, capacitive sensors, MEMS based profilometers, and a variety of other technologies may be adapted to provide indications of proximity, either digital or analog.

Figures 8A, 8B:
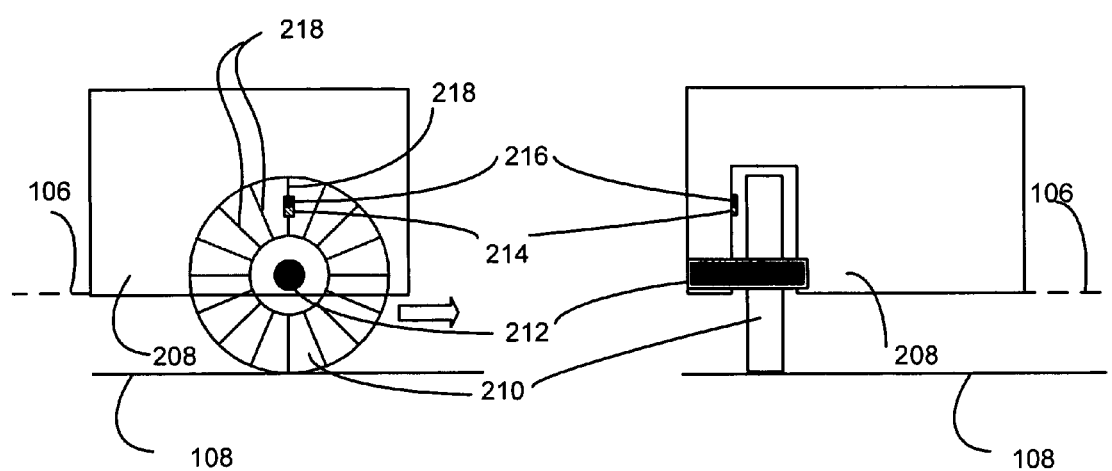
FIGS. 8A and 8B illustrate mechanical-optical motion sensor.

In some embodiments, movement of the depilation device over the skin surface may be detected, and delivery of light duration and intensity controlled taking into account the speed of movement of the depilation device across the skin surface. FIGS. 8A and 8B are side and end views, respectively, of an exemplary optical-mechanical motion sensor. Wheel 210 is mounted with respect to housing 208 by means of axle 212. Housing 208 may be the depilation device housing, or the housing of a motion sensor, which may be mounted in or with respect to the depilation device. Wheel 210 may be mounted at the active surface of the depilation device to detect motion of the depilation device with respect to the skin surface 108. In use, the active surface 106 of the depilation device is positioned close enough to skin surface 108 that wheel 210 contacts skin surface 108. The device may be moved across skin surface 108 in the direction indicated by the arrow in FIG. 8A while maintaining contact between wheel 210 and skin surface 108. Wheel 210 then rotates about axle 212 at a rate dependent upon the rate of motion of the depilation device across the skin surface. Lines 218 (or other detectable indicia) marked on wheel 210 are illuminated by light source 214 and an optical signal is detected from wheel 210 by photodetector 216. Line 218 may be formed of material that differs from other parts of the wheel surface in light reflection, scattering, or absorption properties, such that there is a detectable difference in the optical signal as the line passes under the photodetector.

FIGS. 9A and 9B are side and end views, respectively, of an electromechanical motion sensor. Wheel 227 is mounted with respect to housing 226 by means of axle 228. Housing 226 may be the depilation device housing, or separate motion sensor housing, which may be mounted in or with respect to the depilation device. Wheel 227 may be mounted at the active surface of the depilation device to detect motion of the depilation device with respect to the skin surface 108. In use, the active surface 106 of the depilation device may be positioned close enough to skin surface 108 that wheel 227 contacts skin surface 108. The device may be rolled across skin surface 108 in the direction indicated by the arrow in FIG. 9A while maintaining contact between wheel 227 and skin surface 108. Wheel 227 then rotates about axle 228 at a rate dependent upon the rate of motion of the depilation device across the skin surface. Each line 234 on wheel 227 is formed of a conductive material and connected to lead 236 via contact 237. Brush 232 is mounted on housing 226 and connected to lead 238. As wheel 227 rotates, brush 232 makes an electrical contact with line 234 to close the electrical circuit between lead 236 and lead 238. Leads 236 and 238 may be connected to appropriate electrical circuitry, as known to those of skill in the electrical arts, to permit motion of the depilation device with respect to the skin surface 108 to be detected.

FIG. 10 illustrates an optical motion sensor 241, which includes housing 240, light source 242, and light sensor 244. Optical motion sensor 241 may, for example, function in the same manner as an optical computer mouse, in which light sensor 244 is a CMOS or CCD camera, and comparison of sequentially detected images is used to determine motion. A variety of other optical motion and position sensing technologies may be implemented to provide an indication of movement, position, and/or proximity.

Figure 11:
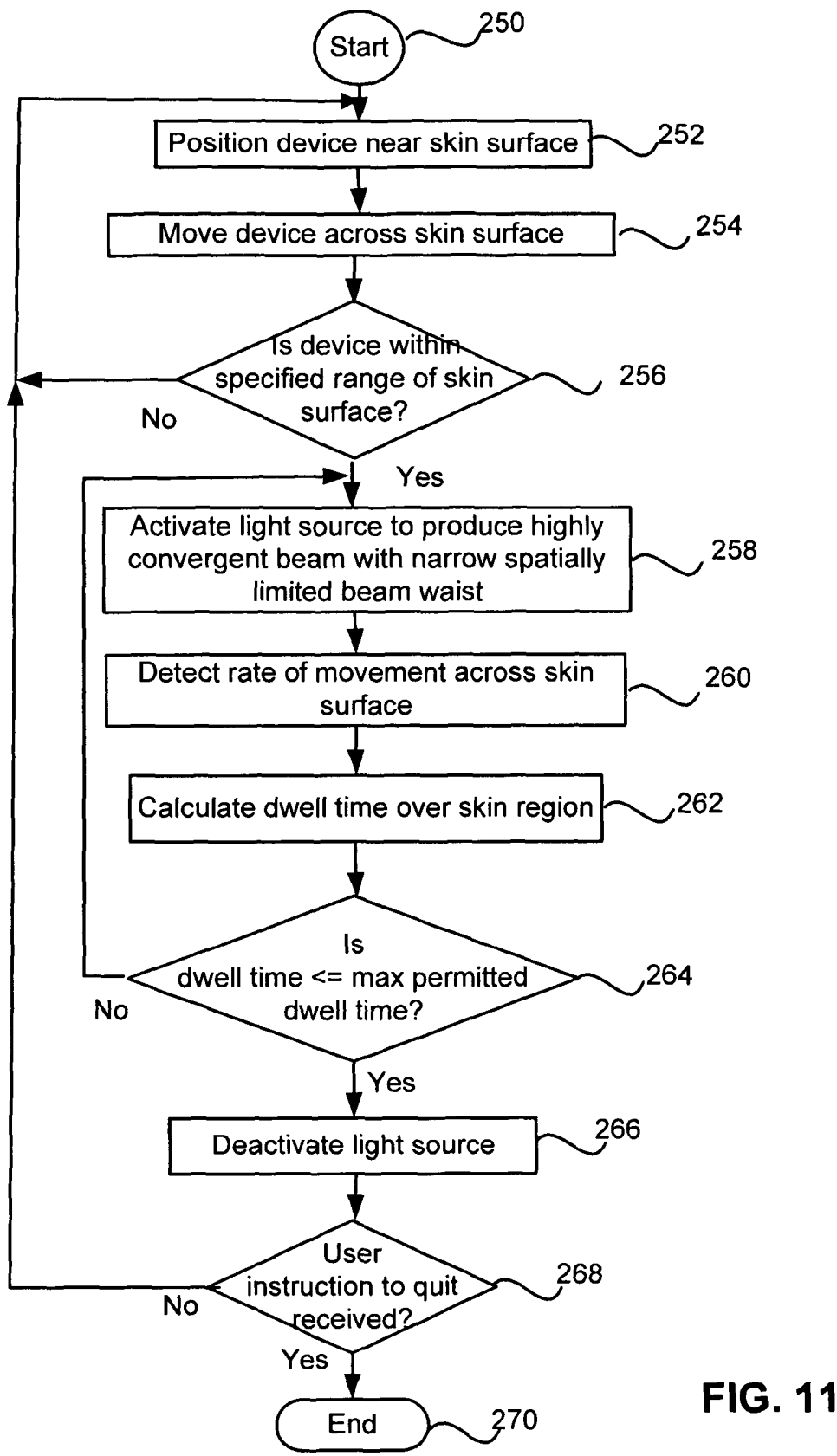
FIG. 11 is a flow diagram depicting an embodiment of a method including motion sensing.

FIG. 11 is a flow diagram of an embodiment of a method of controlling the inventive system to limit the amount of light delivered to a given skin region. This approach may be used, for example, to avoid damage or irritation to the skin. At step 252, the device is positioned near the skin surface. At step 254, the device is moved across the skin surface. At step 256, a determination is made as to whether the device is within a specified distance range of the skin surface. If not, process control returns to step 252, and the step of positioning the device near the skin surface is repeated, following which movement of the device across the skin surface may be continued at step 254. The device position is adjusted until it is determined at step 256 that the device is within the specified distance range of the skin surface. Process control then moves to step 258, where a light source is activated to produce a highly convergent beam with a narrow, spatially limited beam waist. Rate of movement of the device across the skin surface is detected at step 260, and the dwell time of the device over the current skin region is calculated at step 262. If it is determined at step 264 that the calculated dwell time is less than the maximum permitted dwell time, process control returns to step 258, and generation of a convergent beam with a narrow spatially limited beam waist is continued. Detection of rate of movement across the skin surface at step 260 and calculation of the dwell time over the skin region at step 262 are repeated until it is found, at step 264, that the maximum permitted dwell time has been reached or surpassed. The light source is then deactivated at step 266. If a user instruction to quit has been received, as determined at step 268, the process ends. If no quit instruction has been received, process control returns to step 252, the device position is adjusted, and the process continues as described previously, until a user instruction to quit is received.

Figure 12:
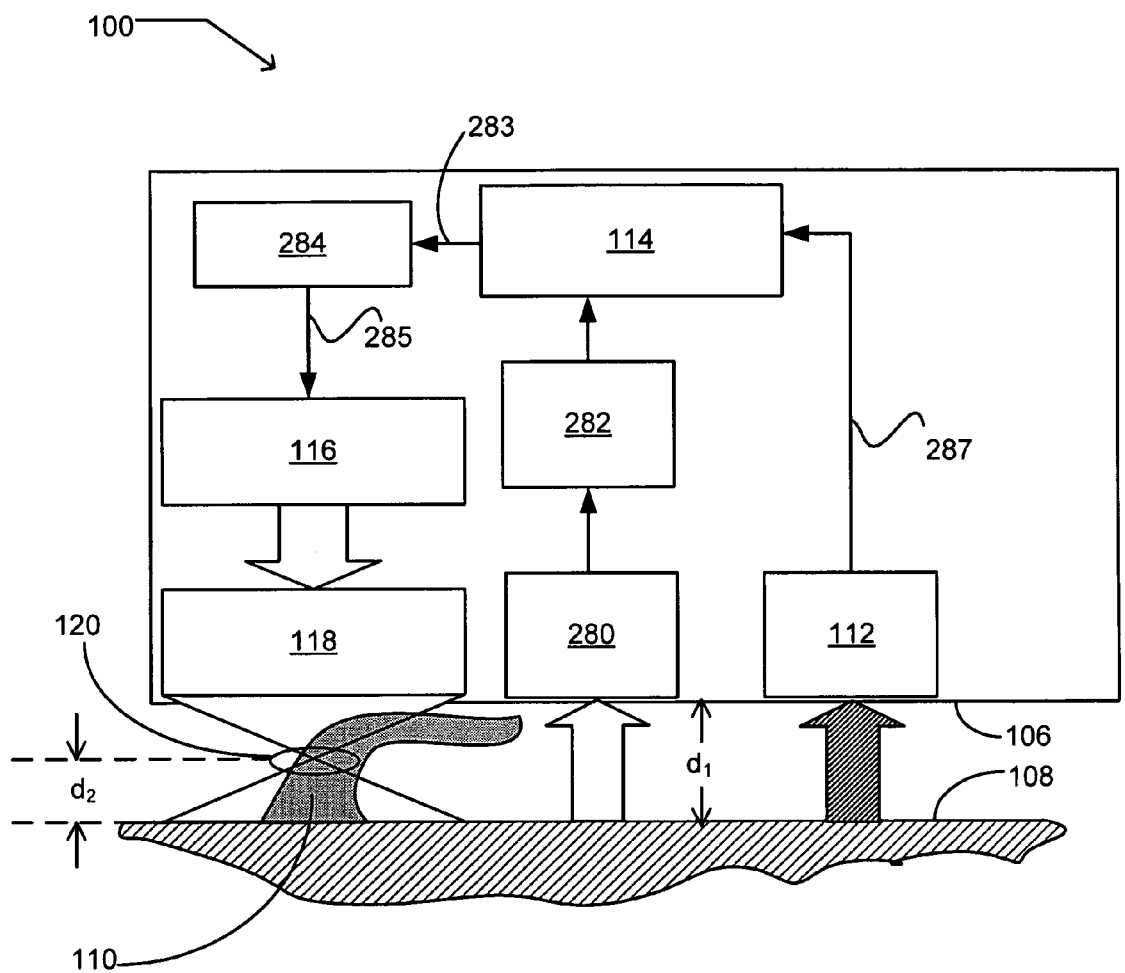
FIG. 12 depicts an exemplary device including image detection.

FIG. 12 illustrates a further embodiment of a depilation device 100. As described previously, device 100 includes a light source 116 and a high numerical aperture lens 118 that modifies light from light source 116 to form a beam that converges to form a narrow beam waist. Device 100 further includes proximity sensor 112 and image detector 280, both of which provide signals to control circuitry 114. Image detector 280 may be, for example, a CMOS or CCD image sensor. Control circuitry 114 generates a driver control signal 283 that is input to light source driver 284, which in turn generates light source drive signal 285. Image detector 280 detects an image of the skin surface, and image analyzer 282 processes the detected image signal to generate information which is utilized by control circuitry 114. Image analyzer 282 may, for example, be configured to identify the presence of one or more hairs on the skin surface, so that light may be targeted to the hairs. Alternatively, image analyzer 282 may be configured to detect other characteristics of the skin which may be used to generate feedback control signals, such as skin color, which may indicate skin irritation (e.g., if redness is detected). Proximity sensor 112 may be any of a number of different types of proximity sensors, including but not limited to the exemplary proximity sensors illustrated in FIGS. 7A-7C. When active surface 106 of depilation device 100 is positioned at a distance $d_1$ from skin surface 108, beam waist 120 is located at a distance $d_2$ from skin surface 108. At this distance, a hair 110 located in the beam may be severed at beam waist 120, providing the light fluence is sufficiently high at the beam waist to melt, vaporize, or otherwise cause sufficient mechanical damage or weakening of the hair shaft. The beam diverges between the beam waist and the skin surface so that the light fluence at the skin surface does not cause damage or irritation to the skin.

Movement of the beam in the X-Y plane through the use of adjustable optical elements, as described previously, and also movement of the beam waist in the Z direction (height or distance above the skin surface) may be used to adjust the beam position with respect to a detected hair shaft, and thus to control the location on the hair shaft on which the beam operates. The beam may cause cutting or mechanical damage to the hair shaft, or may have some other effect (bleaching, coloring, etc.). In some embodiments the effect of the beam may be varied along the length of the hair shaft, e.g. to produce bleaching in a desired pattern or to cause controlled texturing, shaping, coloring, or other effects in a pattern that varies along the length of the hair shaft.

According to one embodiment, a depilation device may include a housing having an active surface, at least one laser source housed within the housing, at least one lens configured to modify light from the laser source, a proximity sensor mounted in the housing, and a laser driver. The lens is configured to modify light from the laser source to produce a beam having a short narrow beam waist of limited spatial extent. The beam exits the active surface such that the beam waist occurs at a first specified distance range from the active surface. The proximity sensor is configured for detecting when the active surface of the housing is within a second distance range from the skin surface, and the laser driver is configured to activate the laser source when the proximity sensor indicates that the active surface is within the second specified distance range. The device may include a microprocessor configured to process at least one sensor signal from the proximity sensor, and to generate a laser drive signal. The first specified distance range may be located just above the skin surface when the active surface is within the second specified distance range. The laser source may include a laser array. The device may include at least one motion sensor capable of detecting motion of the active surface of the device across the skin surface. The motion sensor may include at least one of an optical sensor, an electromechanical sensor, or a mechanical sensor. The laser driver may be configured to activate the laser source when the proximity sensor indicates that the active surface is within a specified range of the skin surface.

Figure 13:
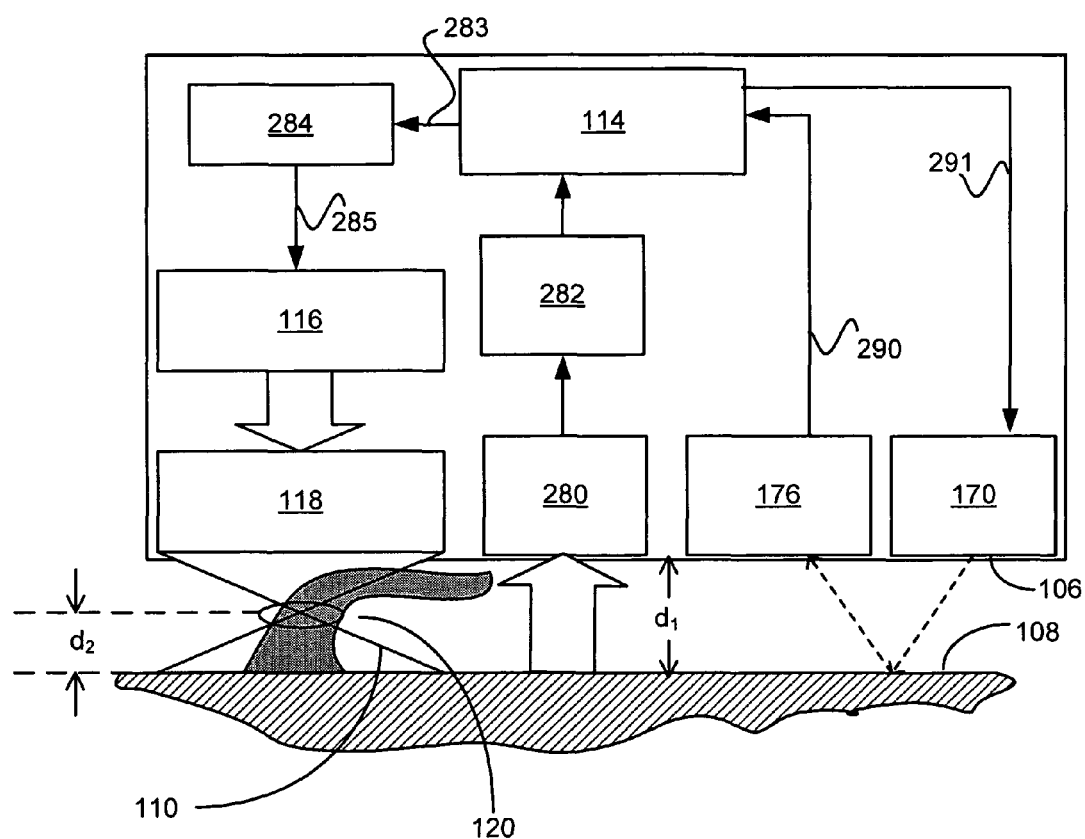
FIG. 13 depicts an exemplary device including a secondary light source.

FIG. 13 depicts a further embodiment of depilation device 100, which includes light source 116, high numerical aperture lens 118, light source driver 284, image detector 280, image analyzer 282, and control circuitry 114, which function substantially as described in connection with FIG. 12. The embodiment of FIG. 13 further includes secondary light source 170 and photodetector 176, which together function as a proximity sensor, as depicted in FIG. 6. A proximity sense signal 290 from photodetector 176 is sent to control circuitry 114, which generates driver control signal 283 for controlling light source driver 284, and secondary control signal 291 for controlling secondary light source 170.

Figure 14:
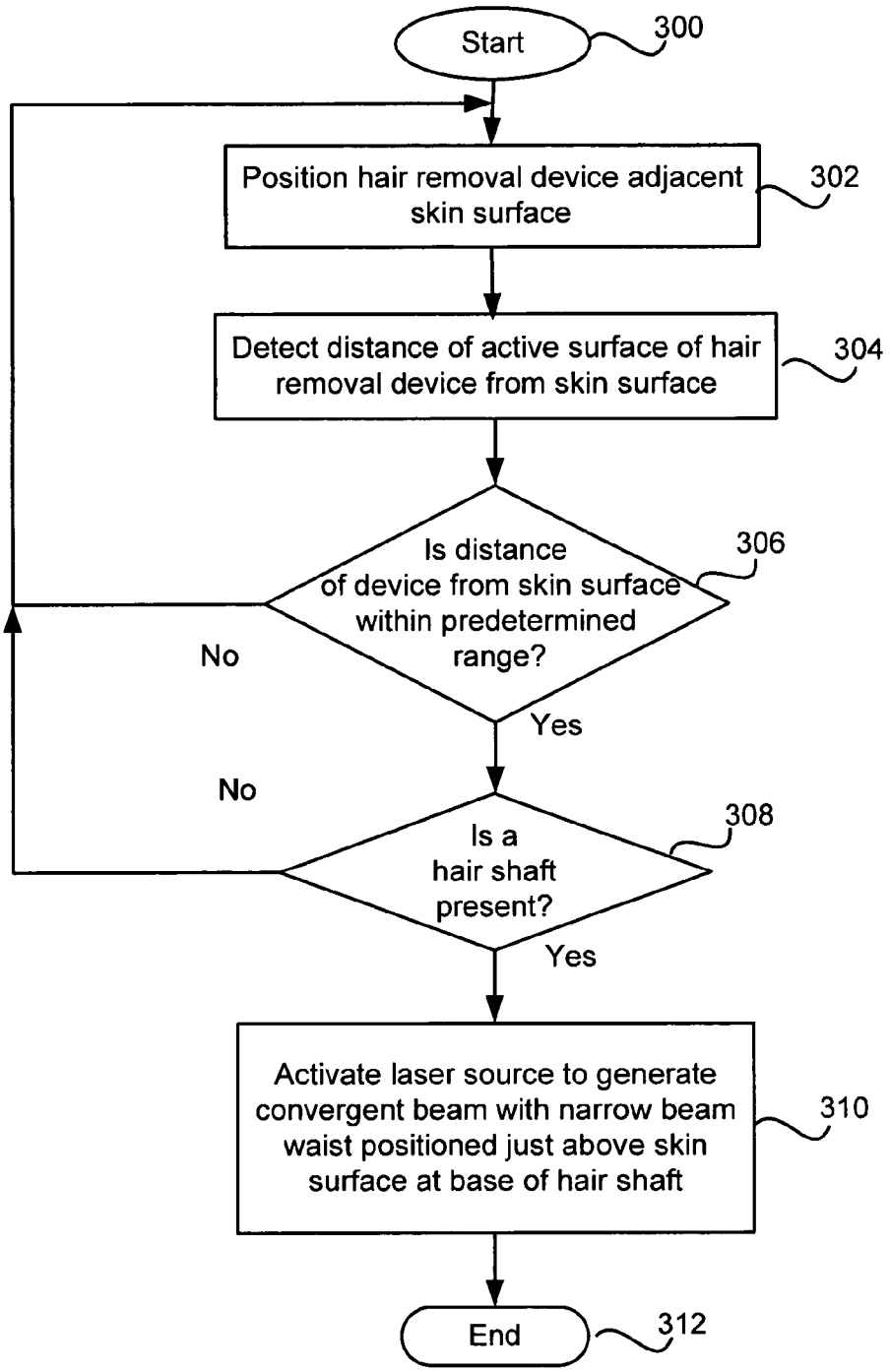
FIG. 14 is a flow diagram for a method including detection of a hair shaft.

FIG. 14 is a flow diagram depicting a control process for use with certain embodiments, e.g., as exemplified in FIGS. 11 and 12, including detecting the presence of a hair shaft prior to activating a laser source. At step 302, a hair removal device is positioned adjacent the skin surface. At step 304, the distance of the active surface of the hair removal device from the skin surface is detected. If the distance of the hair removal device from the skin surface is within a predetermined range, as determined at step 306, and a hair shaft is present, as determined at step 308, at step 310 the laser source is activated to generate a convergent beam with a narrow beam waist positioned just above the skin surface at the base of the hair shaft. If one or both of the conditions tested at steps 306 and 308 are not met, then process control returns to step 302, and the position of hair removal device 203 may be adjusted further. The process of FIG. 14 may be a part of a larger process, and may be repeated multiple times as the hair removal device is moved to different regions of the skin surface. In some embodiments the depilation method may include positioning the beam waist of a highly convergent beam of light on a hair shaft and maintaining the beam waist on the hair shaft for a duration sufficient to cause mechanical failure of the hair shaft. The light of the beam may be comprised of or include a waveband that is absorbed significantly by the hair being processed. The method may include detecting a hair shaft prior to positioning the beam waist on the hair shaft. Positioning the beam waist on the hair shaft may include moving the beam over a skin surface with the beam waist positioned at a desired height relative to the skin surface, with the rate of movement of the beam over the skin surface being such that the beam waist is maintained on a given hair shaft for a duration sufficient to cause mechanical failure of the hair shaft. In general, it is preferred that the duration for which the beam waist is maintained at any given location on the skin is insufficient to cause damage or irritation to the skin surface.

Figure 15A:
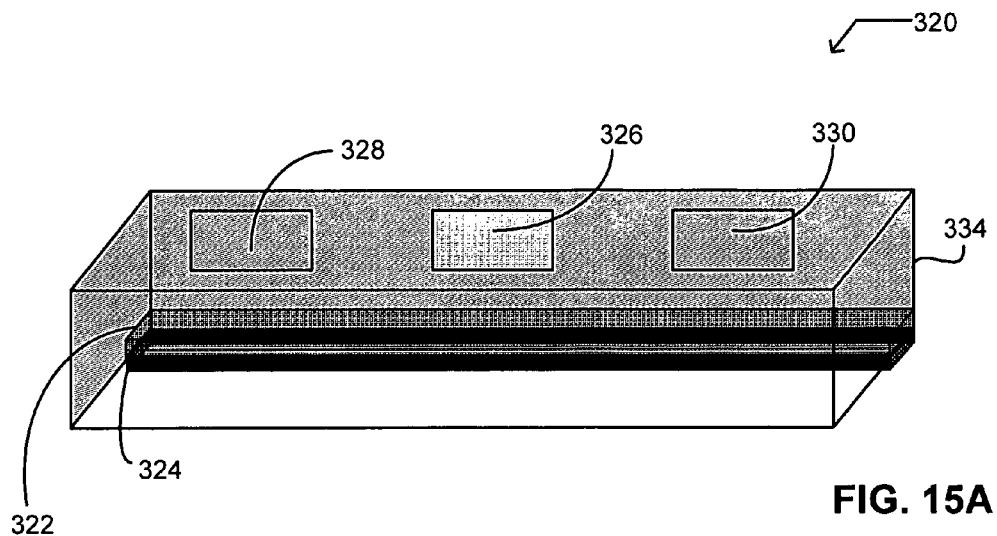
FIG. 15A depicts an exemplary device including a laser bar and lens bar.
Figure 15B:
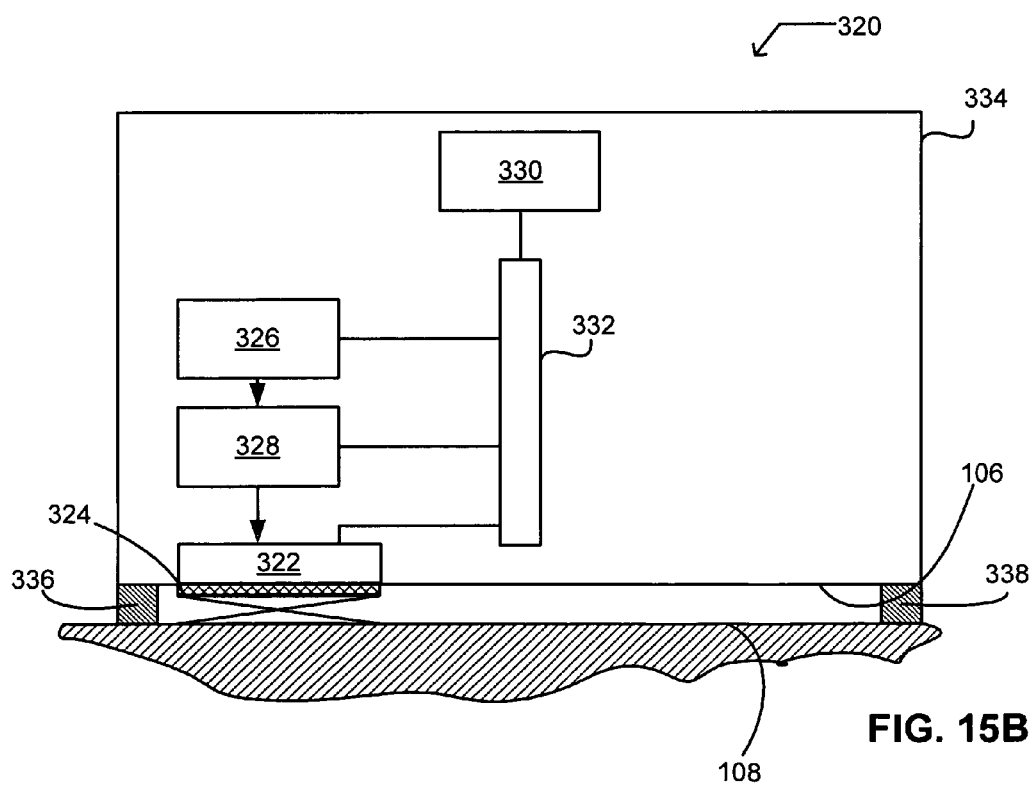
FIG. 15B is a block diagram of the device of FIG. 15A.

In some embodiments, the light source may comprise a single laser. In other embodiments, the light source may comprise a laser array, which may be formed of a plurality of laser diodes or laser sources. FIG. 15A illustrates an embodiment of a handheld depilation device 320 in which a laser bar 322 is used as a light source. Laser bar 322 may be a linear array of laser diodes manufactured as a monolithic semiconductor, according to methods as known by those with skill in the relevant art. Methods of manufacturing laser diode arrays are exemplified by U.S. Pat. Nos. 6,757,309, 6,816,528, 6,829,265, and 6,834,070, all of which are incorporated herein by reference in their entirety. The device may further comprise a plurality of lenses, which may be in the form of a lenslet array. In certain embodiments, one lens may correspond to each laser diode of a plurality of laser diodes. In some embodiments, the optical system may include one or more lenses adjustable in their focal spot-position(s) relative to the immediately-underlying skin-surface or the device housing, or in other operationally-pertinent parameters. Lens bar 324 may be a lenslet array formed by microfabrication techniques as known to those with skill in the art. See, e.g., U.S. Pat. No. 6,757,106, which is incorporated herein by reference in its entirety. Laser bar 322 and lens bar 324 are mounted in housing 334. Also mounted in or on housing 334 are laser drive circuitry 328, controller 326, and power supply 330, as well as optional means for adjusting lens focal-spot position(s). Controller 326 provides a control signal to laser drive circuitry 328, which drives laser bar 322. Power supply 330 may provide power to any or all of laser bar 322, lens bar 324, controller 326 and laser drive circuitry 328. FIG. 15B illustrates the interconnection of components of the device of FIG. 15A. As shown in FIG. 15B, power from power supply 330 may be routed to various system components via power bus 332. FIG. 15B also illustrates the use of spacers 336 and 338 on housing 334, which control, actively or passively or via a combination thereof, how close the active surface 106 of depilation device 320 can be relative to skin surface 108.

In some embodiments, spacers (or stops) 336 and 338 may be used to control the distance between active surface 106 and skin surface 108. In some such embodiments, device control need not depend upon detection or determination of distance or proximity of the device to the skin surface can be omitted. The user may simply place the device against the skin surface and activate a switch to cause the device to produce light. In some embodiments, spacers may include one or more switches that are activated when the device is pressed against a skin surface.

As shown in FIGS. 15A and 15B, a system may be provided for treating a skin region containing one or more hairs that includes a laser array including a plurality of lasers in array, a lens array including a plurality of lenses corresponding to the plurality of lasers, and a detector array including a plurality of photodetectors. The photodetectors are mounted relative to the laser array so that the plurality of photo detectors are able to detect light from the skin region responsive to generation of light by at least a subset of the plurality of lasers when the laser array is brought within a desired distance range for the skin surface. Each of the lenses is positioned with respect to a corresponding laser of the plurality of lasers to modify the profile of the beam generated by the corresponding laser to form a highly convergent beam having a short beam waist. The plurality of lasers may include a plurality of laser diodes or other types of emitters of adequately-focusable radiation of frequency in-or-about the optical portion of the electromagnetic spectrum. The lens array and the laser array may be substantially linear arrays. Although in many embodiments it may be preferable to use a linear array of lenses with a linear array of lasers, one or both of the laser array and the lens array may have a nonlinear organization. For example, array elements could be arranged in a rectangular array configuration, or in some other configuration. In certain embodiments, it may not be necessary that the number of lenses be identical to the number of lasers. Similarly, it is not necessary that the number of detectors be matched to the number of lasers or lenses. The laser array, lens array, and detector array may be positioned relative to each other such that light is detected from the skin region in response to light generation by the subset of the plurality of lasers when the beam waist is positioned just adjacent to the skin surface.

The system illustrated in FIGS. 15A and 15B may include controller 326 configured to receive as input at least one signal indicative of detection of light by the detector array and to generate as output a control signal for driving the laser bar 322. Controller 326 may include at least one of analog circuitry, digital circuitry, and a microprocessor. The detector array may also include a detector bus configured to carry signals from the detector array to the controller. The system may include a drive circuit adapted to receive one or more control signals from the controller and generate one or more drive signals, which are used for driving the plurality of lasers and/or lens adjusters. Lens bar 324 may include a plurality of adjustable lenses in which case controller 326 may be configured to generate a lens control signal for controlling adjustment of the adjustable lenses, and lens bar 324 is configured to receive the lens control signal from the controller. The system may include a secondary illumination source mounted in the mounting member and oriented to provide illumination to substantially the same area as the laser array. The mounting member may form a part of a hand-held device. The system may also include a power source, which may be a battery or various other power sources known to those of skill in the relevant arts.

Figure 16:
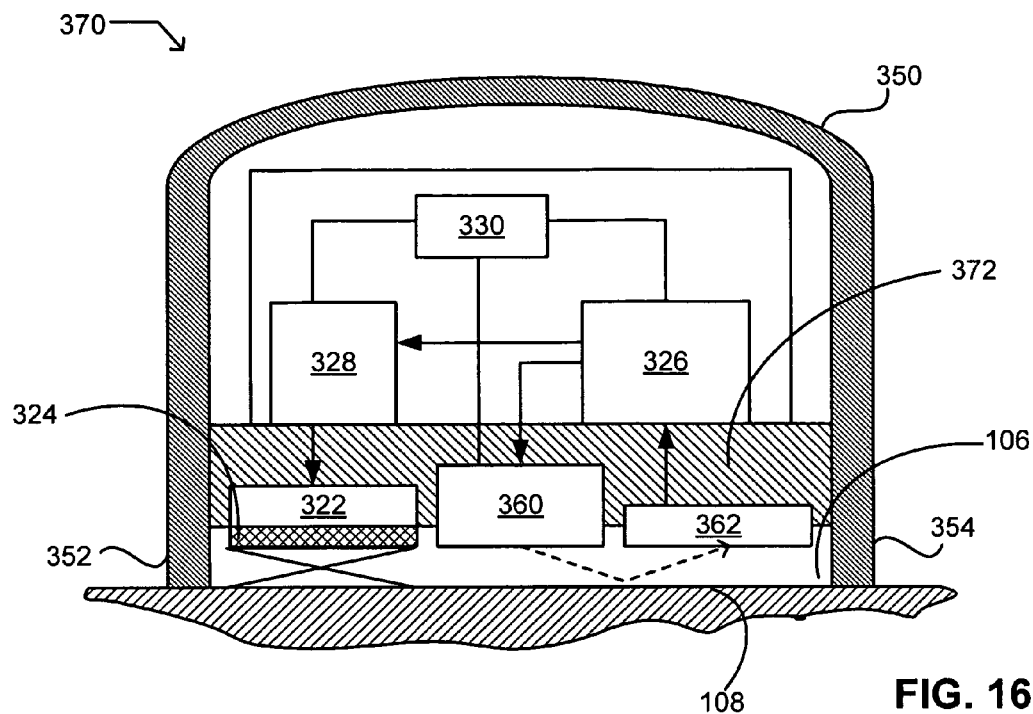
FIG. 16 illustrates a further exemplary embodiment.

FIG. 16 depicts another embodiment of a depilation device 370. The embodiment of FIG. 16 includes housing 350. A mounting member 372, which is positioned in fixed relationship to housing 350, supports laser bar 322, secondary light source 360, and detector bar 362. Secondary light source 360 and detector bar 362 may function to detect one or both of position or motion of the depilation device 370 (and particularly active surface 106) with respect to skin surface 108. Also carried within housing 350 are laser drive circuit 328, controller 326, and power supply 330. Housing 350 includes projecting portions 352 and 354, which function to limit how close active surface 106 of depilation device 370 can come to skin surface 108, as well as to maintain a mean skin-to-device separation-distance, and which may be positioned on the edges of the device, at one or more device-interior points (not shown), or both.

Figure 17:
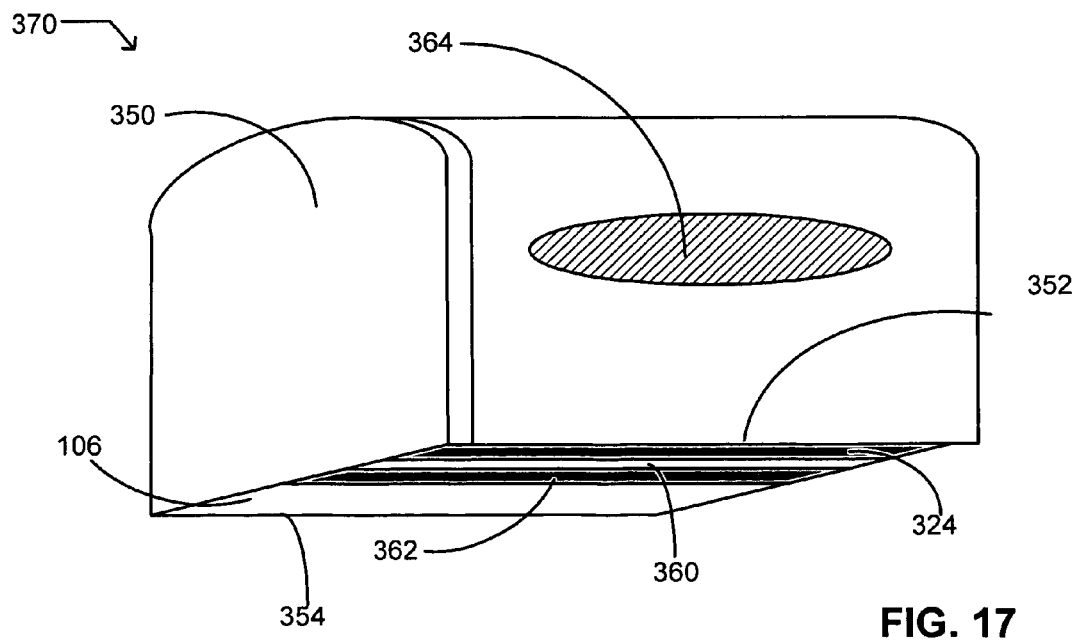
FIG. 17 depicts the external features of an embodiment as depicted in FIG. 16.

FIG. 17 depicts the external features of the depilation device of FIG. 16. Depilation device 370 may include a recessed finger grip 364 in housing 350 to facilitate operation as a hand-held device. Device components visible at active surface 106 include detector bar 362, secondary light source 360, and lens bar 324 (which modifies light from laser bar 322, which is not visible in FIG. 16). According to another embodiment, the hair removal method may include manually positioning a hand-held device containing a laser source adjacent to the skin surface, detecting a distance of the laser source from the skin surface, and if the determined distance is within a specified range, activating the laser source to generate a highly convergent beam of light of a wavelength band absorbed by hair and having a narrow, spatially limited beam waist located at a selected distance above the skin surface.

Figure 18:
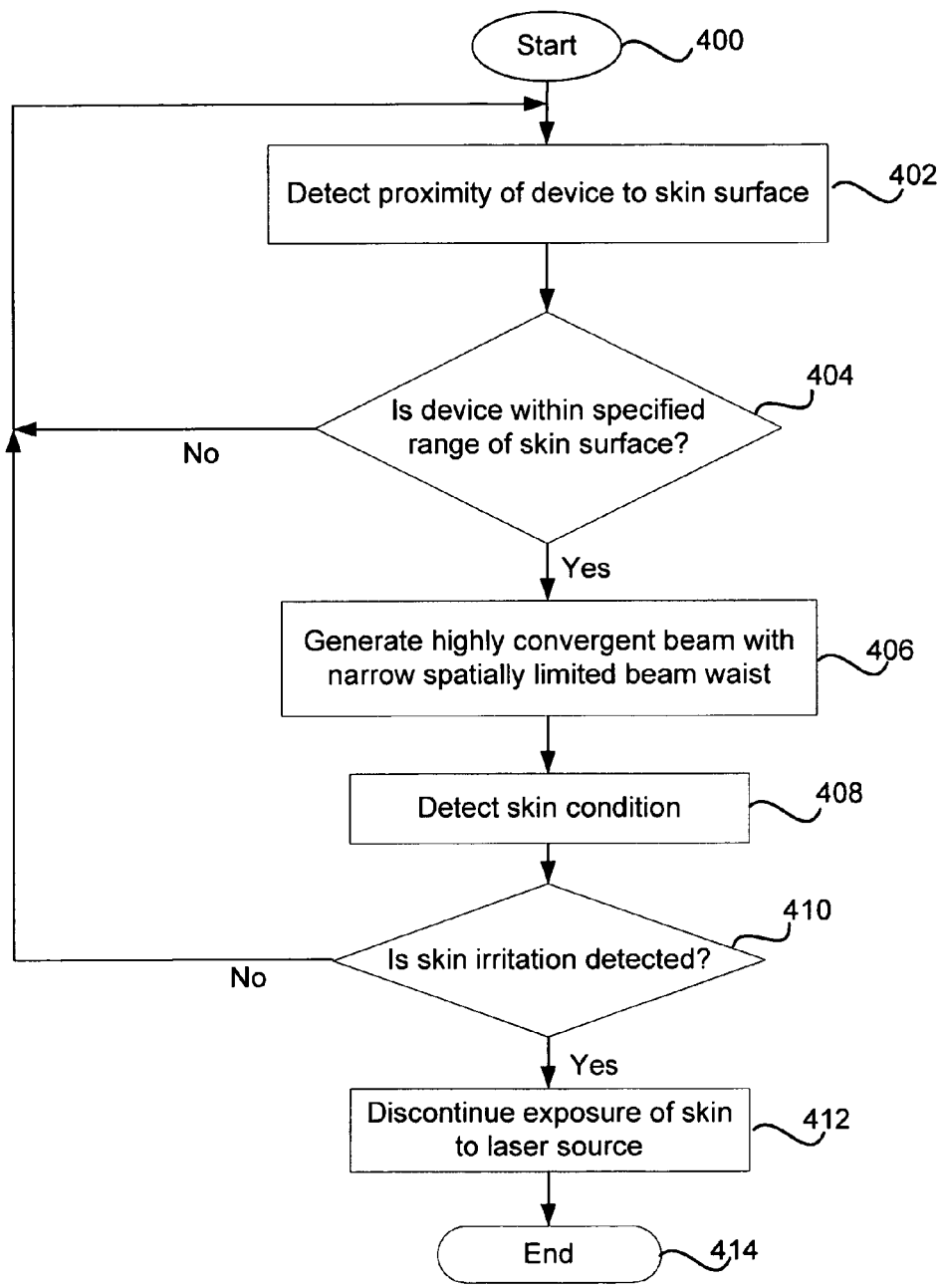
FIG. 18 is a flow diagram of a method including detection of skin condition.

FIG. 18 is a flow diagram depicting a depilation process that includes controlling device operation based upon detected skin condition. At step 402, proximity of the device to the skin surface is detected. If the device is within a specified range of the skin surface, as determined at step 404, a highly convergent beam of light with a narrow, spatially limited beam waist is generated at step 406. If the device is not within the specified range of the skin surface, control returns to step 402, and proximity of the device to the skin surface is monitored until the device is within the specified range of the skin surface. A condition of the skin is detected at step 408. If skin irritation is detected, as determined at step 410, exposure of the skin to the laser source is discontinued at step 412. If no skin irritation is detected at step 410, program control is returned to step 402, and the process as described above is repeated until the device user chooses to discontinue the process.

The method may include discontinuing exposure of the skin region to the beam prior to injury of the skin region by the beam. According to one exemplary method, exposure of the skin region to the beam may be discontinued by moving the hand-held device along the skin surface until it reaches an adjacent skin region. Movement of the device across a skin surface may be continuous or intermittent. Exposure of the skin to the beam may also be discontinued simply by deactivating the laser source, or by blocking the delivery of light from the laser source, for example, through the use of a shuttering or other type of beam-interdiction mechanism.

Figure 19:
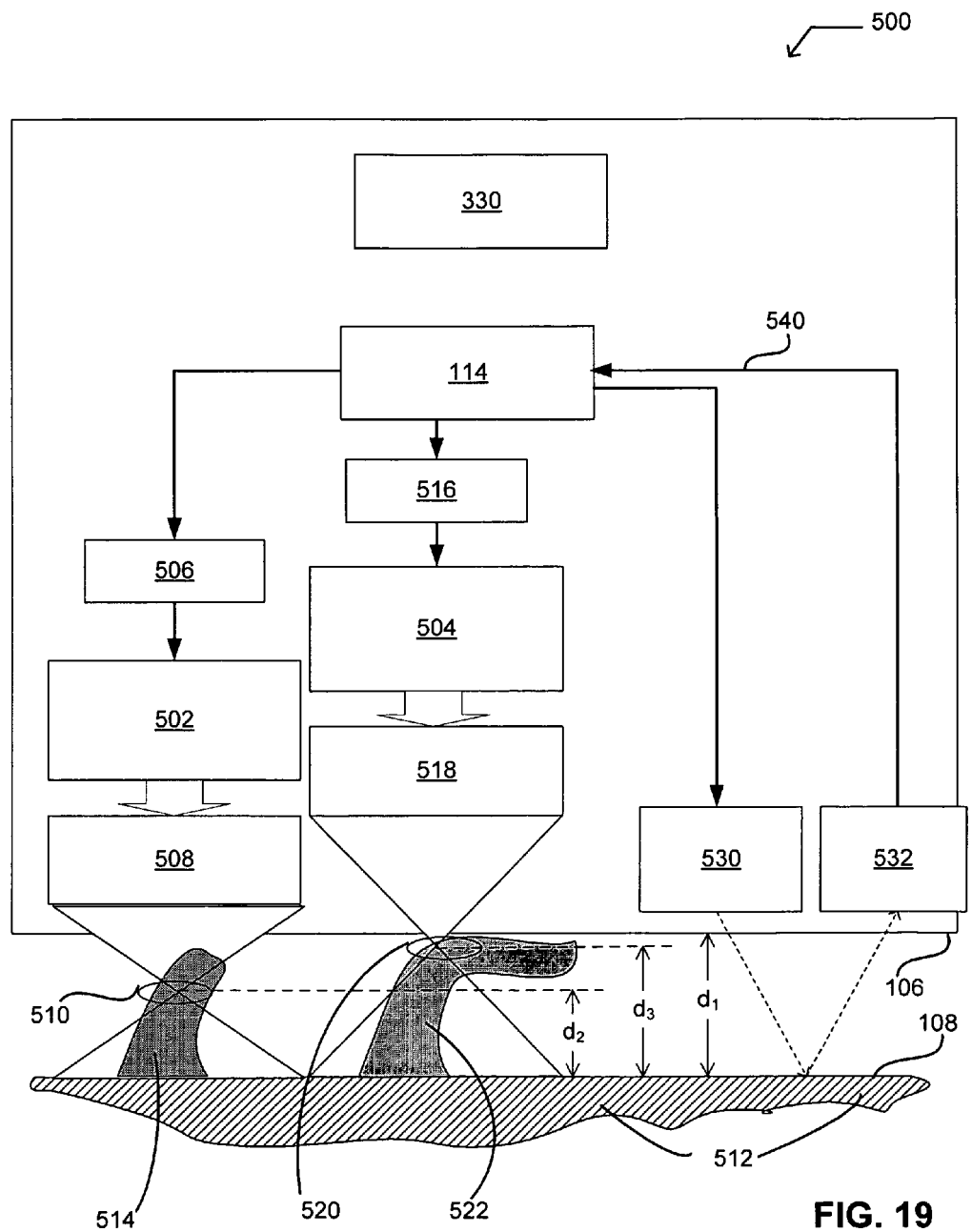
FIG. 19 is a block diagram of an embodiment including light sources focused at different distances from the skin surface.

FIG. 19 is a block diagram depicting a further alternative embodiment of a depilation device 500, including two light sources producing beams with beam waists at different positions with respect to the skin surface. The embodiment of FIG. 19 includes a first light source 502 and second light source 504. First light source driver 506 drives first light source 502 to produce a light beam which is modified by first lens 508 to form a beam which converges to form first beam waist 510. First lens 508 is configured so that when active surface 106 of depilation device 500 is within a distance $d_1$ of skin surface 108, first beam waist 510 will be positioned at a distance $d_2$ from skin surface 108. Second light source driver 516 drives second light source 504 to produce a light beam which is modified by second lens 518 to form a beam which converges to form second beam waist 520. Second lens 518 is configured so that when active surface 106 of depilation device 500 is within a distance $d_1$ of skin surface 108, second beam waist 520 will be positioned at a distance $d_3$ from skin surface 108. In the present example, infrared (IR) source 530 and IR detector 532 are used to detect distance of active surface 106 from skin surface 108. Proximity sense signal 540 is sent to control circuitry 114. Control circuitry 114 produces control signals which are sent to first light source driver 506, second light source driver 516, and IR source 530. In a related embodiment, the two light sources may be two laser arrays. The first laser array and second laser ray may be operable at different optical wavelength bands. Each laser array may have associated therewith a corresponding lens array. The first lens array may be configurable to focus beams produced by the first plurality of lasers at a first distance from the skin region, and the second lens array may be configurable to focus beams produced by the second plurality of lasers at a second distance from the skin region.

Figure 20:
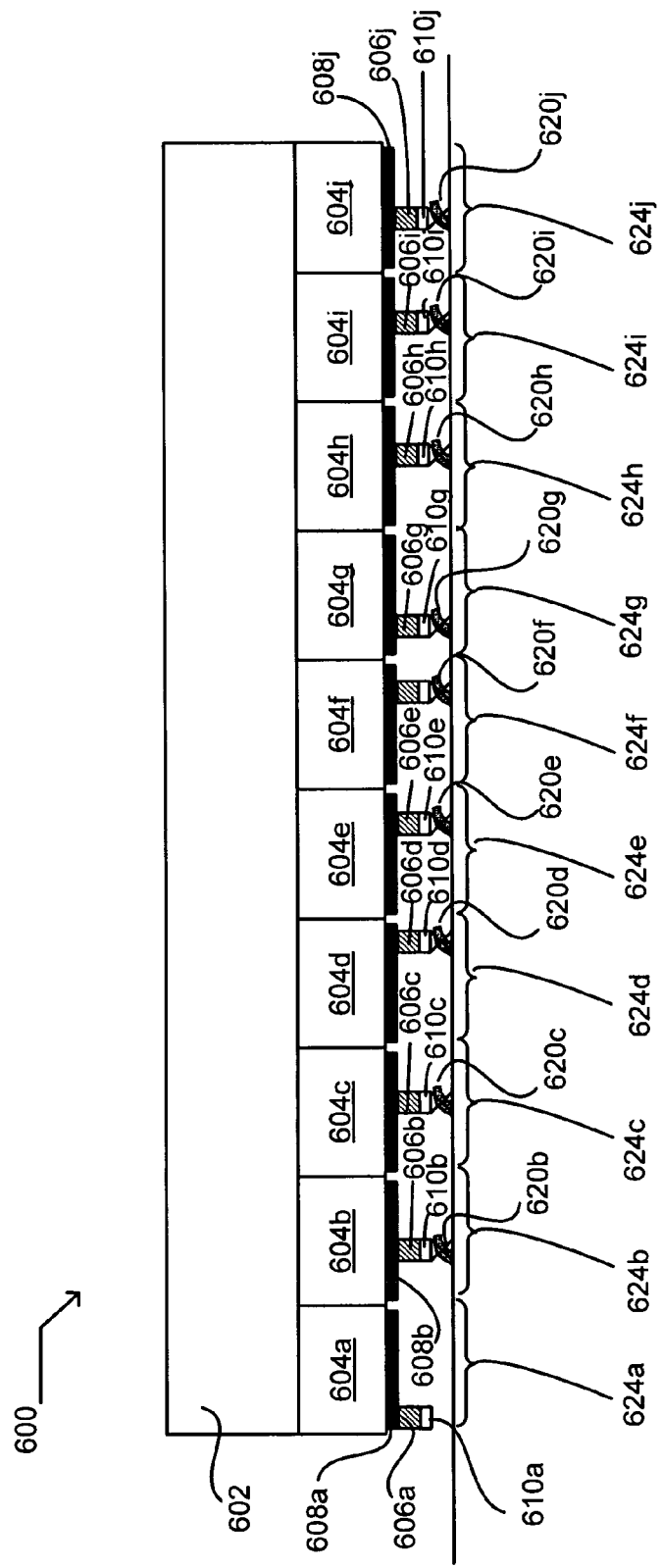
FIG. 20 illustrates an embodiment of a device having a plurality of light sources, each located within a mounting region.

FIG. 20 depicts a further exemplary embodiment of a depilation device 600. Depilation device 600 includes a mounting 602 which includes a plurality of mounting regions 604a, 604b, 604c, 604d, 604e, 604f, 604g, 604h, 604i, and 604j. Light sources 606a-606j, are movably located within mounting regions 604a-604j, respectively. The plurality of mounting regions may be of defined width and arranged in a linear array. Each light source may be of a type that emits light having a waveband absorbed by hair. Each light source 606a-606j may have a lens 610a-610j, respectively, or other optical system or structure, associated therewith to produce a desired beam configuration. Each light source 606a-606j is movable within its corresponding mounting region 604a-604j, with the use of positioner 608a-608j. The device may include a plurality of positioners, each corresponding to one light source and configured to adjust the position of the light source within its corresponding mounting region to direct light from the light source onto a targeted hair shaft. The device may also include one or more optical detectors (not depicted in FIG. 20, but generally as described and illustrated in connection with previous embodiments), configured to detect the presence and location of one or more hair shafts on the skin surface when the depilation device is positioned adjacent the skin surface. When depilation device 600 is positioned over a skin surface 108, each mounting region 604a-604j is positioned over a corresponding skin region 624a-624j. If a hair (e.g. hair 620b) is detected within a skin region (e.g. 624b), the position of the corresponding light source (e.g. 606b) and its associated lens (e.g. 610b) is adjusted so that light from light source 606b is directed toward hair 620b. Each skin region corresponds to one of the plurality of mounting regions. By positioning and activating light sources within multiple mounting regions simultaneously, it is possible to remove hairs from multiple skin regions simultaneously. By moving depilation device 600 across the skin surface 108 in a direction perpendicular to the row of mounting regions, it is possible to depilate a swath of skin that is as wide as the array of mounting regions. The length of the swath will depend on how long, and at what speed, the depilation device 600 is moved over the skin surface. Although in FIG. 20 the plurality of mounting regions is arranged in a substantially linear array, in other embodiments, other arrangements of mounting regions may be used, including two-dimensional arrays and non-linear arrays. Moreover, optical components, such as lenses, scanners, diffractive elements having reflective, refractive or diffractive characteristics, or other components may direct light from one or more of the light sources (e.g., 606b) to spatially distinct locations. The device of FIG. 20 may include a controller configured to drive each positioner in response to detection of one or more hair shafts by one or more optical detectors, and to drive each light source to generate light with an intensity and duration sufficient to produce mechanical failure of each targeted hair shaft. Light sources used in this embodiment may be light-emitting diodes, laser diodes, lasers, or other light sources. Light from each light source is focused by the corresponding lens to form a beam of light that converges to a short narrow beam waist and subsequently diverges. Each light source may be positioned by the positioner to locate the beam waist on a targeted hair shaft at a sufficient distance above the skin so surface that mechanical failure (or other effect of treatment) of the hair shaft occurs at the beam waist without the production of damage or irritation at the skin surface.

Figure 21:
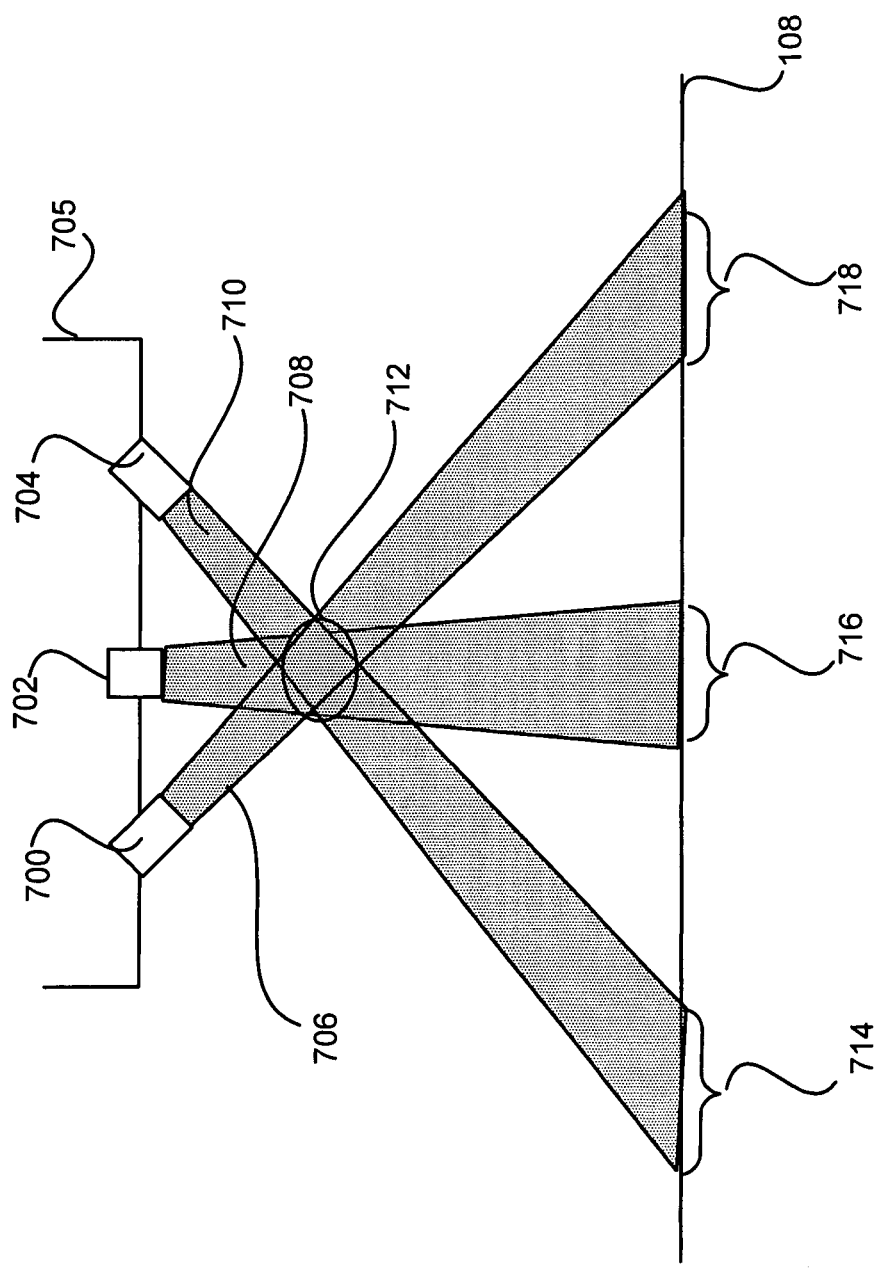
FIG. 21 illustrates an embodiment using overlapping beams.

In another alternative embodiment, instead of generating a convergent beam having a short, narrow beam waist, a depilation device may produce multiple beams of light that overlap to produce a high fluence overlap region having fluence sufficient to sever or produce mechanical damage to or failure of a hair shaft. In the example shown in FIG. 21, three light sources 700, 702, and 704 mounted in depilation device 705 are used. Beams 706, 708, and 710 from light sources 700, 702 and 704, respectively, overlap to form overlap region 712. The light sources are aimed so that light from the light sources overlaps spatially at an overlap region located at a desired distance above the skin surface. The light fluence at the overlap region may be controlled such that it is sufficient to cause mechanical failure of a hair within the overlap region, while light from the light sources striking the skin surface (e.g. at regions 714, 716, and 718) is sufficiently nonoverlapping that the light fluence at the skin surface is below the threshold for causing tissue damage or irritation. Light fluence at the overlap region may be sufficient to cause absorption of between about 50 and about 200 joules per gram by hair at the overlap region. In some embodiments, light fluence at the overlap region may be sufficient to cause absorption of between about 50 and about 100 joules per gram by hair at the overlap region. As depicted in FIG. 21, it is not necessary that the beams (e.g., 706, 708, and 710) be focused to form a converging beam if overlap of multiple beams is used to produce a sufficiently high light fluence at the overlap region. Individual beams may diverge, providing the fluence at the overlap region is sufficiently high to cause mechanical weakening or failure of the hair, while the fluence at the skin surface is low enough to avoid causing damage or irritation to the skin. However, in some embodiments it may be desirable to utilize individual light beams that are focused to form a beam waist, with the beams oriented so that the overlap occurs substantially at the beam waist(s) of one or more individual beams. Various numbers and configurations of light sources may be used to produce an overlap region. The system of FIG. 21 is merely exemplary, and overlap of any number of beams, from two or more, may be used in various embodiments. Surface and target sensing, signal analysis, device powering, and control of light sources may operate generally as described previously in connection with other embodiments.

In the broadest terms, a set of multiple light sources, which converge to an overlap region, as depicted in FIG. 21, or a single light source used in combination with suitable optics to generate a convergent beam with a narrow beam waist, can both be considered sources of convergent light with a restricted high fluence region. Appropriately configured, these different light source configurations may be substantially functionally equivalent for certain applications.

With regard to the hardware and/or software used in the control of depilation systems according to the present image, and particularly to the sensing, analysis, and control aspects of such systems, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for detection or sensing, signal processing, and device control in the fashion set forth herein, and thereafter use standard engineering practices to integrate such described devices and/or processes into depilation systems as exemplified herein. That is, at least a portion of the devices and/or processes described herein can be integrated into a depilation system via a reasonable amount of experimentation.

Those having skill in the art will recognize that systems as described herein may include one or more of a memory such as volatile and non-volatile memory, processors such as microprocessors and digital signal processors, computational-supporting or—associated entities such as operating systems, user interfaces, drivers, sensors, actuators, applications programs, one or more interaction devices, such as data ports, control systems including feedback loops and control implementing actuators (e.g., devices for sensing position and/or velocity and/or acceleration or time-rate-of-change thereof; control motors for moving and/or adjusting components). A depilation system may be implemented utilizing any suitable available components, such as those typically found in appropriate computing/communication systems, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of adjustable lens system configuration and image detector configuration may be within the scope of the invention. As has been discussed, the choice of system configuration may depend on the intended application of the system, the environment in which the system is used, cost, personal preference or other factors. Display design, manufacture, and control processes may be modified to take into account choices of display element components and configuration, and such modifications, as known to those of skill in the arts of display design and construction, may fall within the scope of the invention. Therefore, the full spirit or scope of the invention is defined by the appended claims and is not to be limited to the specific embodiments described herein.

The invention claimed is:

1. A depilation method comprising:
   a) detecting or determining proximity of a depilation device to a skin surface;
   b) responsive to detecting or determining proximity of a depilation device to a skin surface, delivering a beam of highly convergent light from said depilation device to the skin surface, said beam of light having a beam waist positioned substantially at a base of at least one hair shaft;
   c) delivering said light for a duration and with an intensity sufficient to cause mechanical failure of the at least one hair shaft at said beam waist; and
   d) delivering a beam of light having a diameter at the skin surface that is between about 2 and about 10 times the diameter of said beam at said beam waist.

2. The method of claim 1, wherein detecting proximity of said depilation device to the skin surface includes determining that said depilation device is within a predetermined distance range of the skin surface.

3. The method of claim 1, including delivering a beam of light having an angle of convergence of between about 25 and about 70 degrees relative to the axis of said beam.

4. The method of claim 1, including delivering a beam of light having a beam waist positioned between about 40 μm and about 300 μm above the skin surface.

5. The method of claim 1, including delivering a beam of light having a beam waist diameter of between about 17 μm and about 600 μm.

6. The method of claim 1, including detecting movement of said depilation device across the skin surface, wherein delivering said light for a duration and intensity sufficient to cause mechanical failure of said at least one hair shaft includes taking into account the speed of movement of said depilation device across the skin surface.

7. The method of claim 1, including delivering said beam of light to said skin surface through a light-conducting medium interposed between said depilation device and said skin surface.

8. A depilation device comprising:
   a) a light source capable of producing light of a wavelength band significantly absorbed by hair;
   b) a lens positioned to receive light from the light source and configured to form from the received light a highly convergent beam having a narrow, spatially limited beam waist;
   c) a proximity sensor capable of detecting the proximity of said light source to a skin surface and generating a proximity sense signal indicative of said proximity; and
   d) control circuitry configured to gate said light in response to said proximity sense signal, wherein said control circuitry is configured to permit generation of said highly convergent beam such that said narrow spatially limited beam waist is positioned within a distance-range of about 40 μm and about 300 μm above the skin surface.

9. The depilation device of claim 8, wherein said lens has a numerical aperture of between about 0.64 and about 0.87.

10. The depilation device of claim 8, wherein said lens has an f-number of between about 1.68 and about 3.46.

11. The depilation device of claim 8, wherein said light source comprises a laser, a laser diode, or a light-emitting diode.

12. The depilation device of claim 8, configured as a handheld device, said handheld device comprising a handset containing said light source, said lens, said proximity sensor, and said control circuitry.

13. The method of claim 1, wherein said light is delivered as one or more pulses.

14. The method of claim 2, including detecting proximity of said depilation device to the skin surface with one of an optical sensor, a mechanical sensor, an electromechanical sensor, an acoustic sensor, and a capacitive sensor and delivering said light to said skin surface only when said depilation device, and delivering said beam of highly convergent light only when said depilation device is within said predetermined distance range of the skin surface.

15. The depilation device of claim 8, including a handset containing a high numerical aperture lens and said proximity sensor, a base unit containing said light source, and an optical linkage between said base unit and said handset configured to transmit light from said light source to said high numerical aperture lens, wherein said control circuitry is located in at least one of said handset and said base unit connected to said handset by at least one of an electrical connection, an optical connection, or a wireless connection.

* * * * *